(12) United States Patent
Iguchi et al.

(10) Patent No.: US 10,974,062 B2
(45) Date of Patent: Apr. 13, 2021

(54) PHOTOIRRADIATION SUBSTRATE

(71) Applicants: SHARP KABUSHIKI KAISHA, Osaka (JP); OSAKA CITY UNIVERSITY, Osaka (JP); SBI PHARMACEUTICALS CO., LTD., Tokyo (JP)

(72) Inventors: Katsuji Iguchi, Sakai (JP); Hiroya Sato, Sakai (JP); Takashi Yoshimoto, Sakai (JP); Jun Mori, Sakai (JP); Toshiyuki Ozawa, Osaka (JP); Kunio Awazu, Suita (JP)

(73) Assignees: SHARP KABUSHIKI KAISHA, Osaka (JP); OSAKA CITY UNIVERSITY, Osaka (JP); SBI PHARMACEUTICALS CO.. LTD., Tokyo (JP)

( * ) Notice: Subject to any disclaimer, the term of this patent is extended or adjusted under 35 U.S.C. 154(b) by 209 days.

(21) Appl. No.: 16/311,527

(22) PCT Filed: Jun. 21, 2017

(86) PCT No.: PCT/JP2017/022769
§ 371 (c)(1),
(2) Date: Dec. 19, 2018

(87) PCT Pub. No.: WO2017/221950
PCT Pub. Date: Dec. 28, 2017

(65) Prior Publication Data
US 2019/0321653 A1    Oct. 24, 2019

(30) Foreign Application Priority Data
Jun. 24, 2016 (JP) .............................. JP2016-126081

(51) Int. Cl.
*A61N 5/06* (2006.01)

(52) U.S. Cl.
CPC .... *A61N 5/0616* (2013.01); *A61N 2005/0645* (2013.01); *A61N 2005/0652* (2013.01)

(58) Field of Classification Search
None
See application file for complete search history.

(56) References Cited

U.S. PATENT DOCUMENTS

| 5,616,140 A | 4/1997 | Prescott |
| 5,913,883 A | 6/1999 | Alexander et al. |

(Continued)

FOREIGN PATENT DOCUMENTS

| JP | 2005-031629 A | 2/2005 |
| JP | 2006-289055 A | 10/2006 |

(Continued)

*Primary Examiner* — Zandra V Smith
*Assistant Examiner* — Lawtence C Tynes, Jr.
(74) *Attorney, Agent, or Firm* — ScienBiziP, P.C.

(57) ABSTRACT

The present invention includes: a front-side positive trace (2P) disposed on a flexible substrate (5); a positive external connection line (12P) connected to the front-side positive trace (2P) to supply electric power; and LED chips (4) provided to the flexible substrate (5) and connected to the front-side positive trace (2P), wherein an electric resistance between the positive external connection line (12P) and one of the LED chips (4) which is farthest from the positive external connection line (12P) is less than an internal resistance of the one of the LED chips (4).

19 Claims, 15 Drawing Sheets

(56) References Cited

U.S. PATENT DOCUMENTS

| | | |
|---|---|---|
| 2004/0257359 A1 | 12/2004 | Muroi et al. |
| 2007/0241349 A1 | 10/2007 | Kishioka |
| 2012/0125169 A1* | 5/2012 | Suda .................. B23K 26/032 83/73 |
| 2013/0035629 A1* | 2/2013 | Soltz ...................... A61L 15/44 604/20 |
| 2013/0041434 A1* | 2/2013 | Youn .................. A61N 5/0625 607/90 |
| 2013/0087368 A1 | 4/2013 | Imai et al. |
| 2014/0062316 A1* | 3/2014 | Tischler ................ F21V 21/14 315/185 R |
| 2018/0043177 A1 | 2/2018 | Iguchi et al. |

FOREIGN PATENT DOCUMENTS

| | | |
|---|---|---|
| JP | 2007-287842 A | 11/2007 |
| JP | 2011-152714 A | 8/2011 |
| JP | 2013-093557 A | 5/2013 |
| JP | 2015-177031 A | 10/2015 |
| JP | 2016-054267 A | 4/2016 |
| WO | 01/14012 A1 | 3/2001 |
| WO | 2008/144157 A1 | 11/2008 |
| WO | 2012/023086 A1 | 2/2012 |
| WO | 2015/016007 A1 | 2/2015 |
| WO | 2016/136340 A1 | 9/2016 |

\* cited by examiner

1: IRRADIATION SUBSTRATE
2P: FRONT-SIDE POSITIVE TRACE
5: FLEXIBLE SUBSTRATE

2P: FRONT-SIDE POSITIVE TRACE
2N: FRONT-SIDE NEGATIVE TRACE
4: LED CHIP
5: FLEXIBLE SUBSTRATE
8: FRONT-AND-BACK CONNECTING PORTION

2P: FRONT-SIDE POSITIVE TRACE
2N: FRONT-SIDE NEGATIVE TRACE
4: LED CHIP
5: FLEXIBLE SUBSTRATE
8: FRONT-AND-BACK CONNECTING PORTION
9N: BACK-SIDE NEGATIVE TRACE

12P: POSITIVE EXTERNAL CONNECTION LINE
12N: NEGATIVE EXTERNAL CONNECTION LINE
23: IRRADIATION SUBSTRATE

2P: FRONT-SIDE POSITIVE TRACE
2N: FRONT-SIDE NEGATIVE TRACE
4: LED CHIP
8: FRONT-AND-BACK CONNECTING PORTION

2P: FRONT-SIDE POSITIVE TRACE
2N: FRONT-SIDE NEGATIVE TRACE
4: LED CHIP
5: FLEXIBLE SUBSTRATE
8: FRONT-AND-BACK CONNECTING PORTION
9N: BACK-SIDE NEGATIVE TRACE

PHOTOIRRADIATION SUBSTRATE

TECHNICAL FIELD

The present invention relates to an irradiation substrate for use in phototherapy, in which light is applied to a treatment target area of the skin of mainly a human being or an animal, or in hairdressing and cosmetology.

BACKGROUND ART

Phototherapy has been used for a variety of purposes such as for treating diseases like neonatal jaundice, psoriasis, and acne, for relieving pain, and for cosmetic purposes. In phototherapy, a variety of light sources are used selectively depending on the purpose. For example, in a case where a light source is an excimer lamp, an arc lamp, or the like, a treatment target area is placed at a certain distance from the fixed light source and light is applied. However, with this technique, the light is shone also on the other area other than the treatment target area, and therefore some measure to, for example, cover the other area with a light blocking object is needed, such as an eye mask for protecting the eyes. Furthermore, a patient is fixed in an immovable position for several tens of minutes, which is not a favorable experience although this is necessary for treatment. Furthermore, for curved surface parts such as arms and legs, irradiation intensity on the treatment target area varies from one position of the treatment target area to another depending on the angle and distance to the light source, and therefore it is difficult to apply light to the treatment target area in a uniform manner. In addition, such a lamp-type apparatus is large in size and has a lot of attachment devices such as an electric power source and a cooling device. Thus, such an apparatus requires a large installation area, occupies a large space, and is also costly.

On the other hand, when a laser is used as a light source, light emitted from the light source is in the form of a spot. This necessitates scan-irradiation of a treatment target area when the treatment target area is large, and requires complicated, expensive equipment.

In regard to an apparatus that makes use of optical fibers to shine light in the form of a plane, light is supplied into the fibers with a relatively low efficiency, and therefore the resulting irradiation power is inevitably low. As such, such an apparatus is suitable only for relatively long-term treatment.

In view of such circumstances, there has been a demand for a flexible light source for irradiation that is capable of covering a treatment target area along the treatment target area at a constant distance from the treatment target area. In order to meet such a demand, some ideas have been proposed; however, none of them have been realized or developed to the extent that they can be used widely.

The above ideas, which have been disclosed, are as follows.

Patent Literature 1 discloses an irradiation apparatus in which a laser and a light emitting diode (LED) as light emission sources are disposed on a flexible substrate and which is designed to be used such that the flexible substrate is wrapped around a treatment target area.

Patent Literature 2 discloses an irradiation apparatus for facial treatment, in which an LED as a light emission source is disposed on a flexible substrate and which is designed to be used such that the flexible substrate covers a user's face.

Patent Literature 3 discloses a flexible irradiation apparatus in which many LEDs as light emission sources are disposed on a flexible substrate and which is designed to carry out irradiation such that the flexible substrate is wrapped around a treatment target area.

Patent Literature 4 discloses an irradiation apparatus designed for application to a user's head, in which an LED as a light emission source is disposed on the inside of a cap.

Patent Literature 5 discloses an irradiation apparatus in which an LED as a light emission source is disposed on a flexible substrate and a light transmitting material is sandwiched between a treatment target area and the LED, and thereby heat generated from the LED is transferred to the treatment target area.

There has been a demand for an irradiation apparatus designed to treat a relatively small (regional) treatment target area of about several centimeters which many people suffer, such that: light is applied to the treatment target area while covering only the treatment target area; and thereby the degree of fixing of a patient is reduced and least burden is placed on the patient. With such a light source, patients can receive treatment without regular visits to the hospital.

CITATION LIST

Patent Literature

[Patent Literature 1]
Specification of U.S. Pat. No. 5,616,140 (Registration date: Apr. 1, 1997)
[Patent Literature 2]
Specification of U.S. Pat. No. 5,913,883 (Registration date: Jun. 22, 1999)
[Patent Literature 3]
Pamphlet of PCT International Publication No. WO2001/14012 (Publication Date: Mar. 1, 2001)
[Patent Literature 4]
Pamphlet of PCT International Publication No. WO2008/144157 (Publication Date: Nov. 27, 2008)
[Patent Literature 5]
Pamphlet of PCT International Publication No. WO2012/023086 (Publication Date: Feb. 23, 2012)

SUMMARY OF INVENTION

Technical Problem

However, the conventional techniques described above have the following issues.

In order to apply light to a treatment target area of a certain size in a uniform manner in phototherapy, it is more preferable to arrange a large number of relatively low-power LED chips on a surface of a flexible substrate than using a small number of high-power LED chips.

However, if a large number of LED chips are arranged on the surface of a flexible substrate, some LED chips are connected by long traces to an electric power supply part (which is provided to the flexible substrate to externally supply electric power), whereas other LED chips are connected by short traces to the electric power supply part. There is large electric resistance between the electric power supply part and the LED chips connected by long traces to the electric power supply part, whereas there is small electric resistance between the electric power supply part and the LED chips connected by short traces to the electric power supply part.

This causes a difference between electric current passing through the LED chips connected by long traces to the electric power supply part and electric current passing through the LED chips connected by short traces to the electric power supply part, resulting in variations in emission intensity among the foregoing large number of LED chips. This results in non-uniform irradiation intensity of an irradiation substrate.

The present invention was made in view of the above issues, and an object thereof is to provide an irradiation substrate which is capable of bringing irradiation intensity closer to uniform.

Solution to Problem

In order to attain the above object, an irradiation substrate in accordance with one aspect of the present invention includes: a trace disposed on a flexible substrate; an electric power supply part connected to the trace to externally supply electric power; and LED chips disposed on a front side of the flexible substrate and connected to the trace, wherein an electric resistance between the electric power supply part and one of the LED chips which is farthest from the electric power supply part is less than an internal resistance of the one of the LED chips which is farthest from the electric power supply part.

In order to attain the above object, another irradiation substrate in accordance with one aspect of the present invention includes: a trace disposed on a flexible substrate; an electric power supply part connected to the trace to externally supply electric power; and LED chips provided to the flexible substrate and connected to the trace, wherein the LED chips are substantially equal to each other in electric resistance between itself and the electric power supply part.

In order to attain the above object, a further irradiation substrate in accordance with one aspect of the present invention includes: a trace disposed on a flexible substrate; an electric power supply part connected to the trace to externally supply electric power; and LED chips provided to the flexible substrate and connected to the trace, wherein an electric resistance between the electric power supply part and one of the LED chips which is disposed near a center of the flexible substrate is greater than an electric resistance between the electric power supply part and another one of the LED chips which is disposed near a periphery of the flexible substrate.

Advantageous Effects of Invention

One aspect of the present invention brings about an effect of making it possible to provide an irradiation substrate which is capable of bringing irradiation intensity closer to uniform.

DESCRIPTION OF EMBODIMENTS

The following description will discuss embodiments of the present invention in detail.

Embodiment 1

The following description will discuss Embodiment 1 of the present invention with reference to FIGS. 1 to 8. For convenience of description, members having functions identical to those described in a certain embodiment are assigned identical referential numerals and their descriptions may be omitted.

Figure 1:
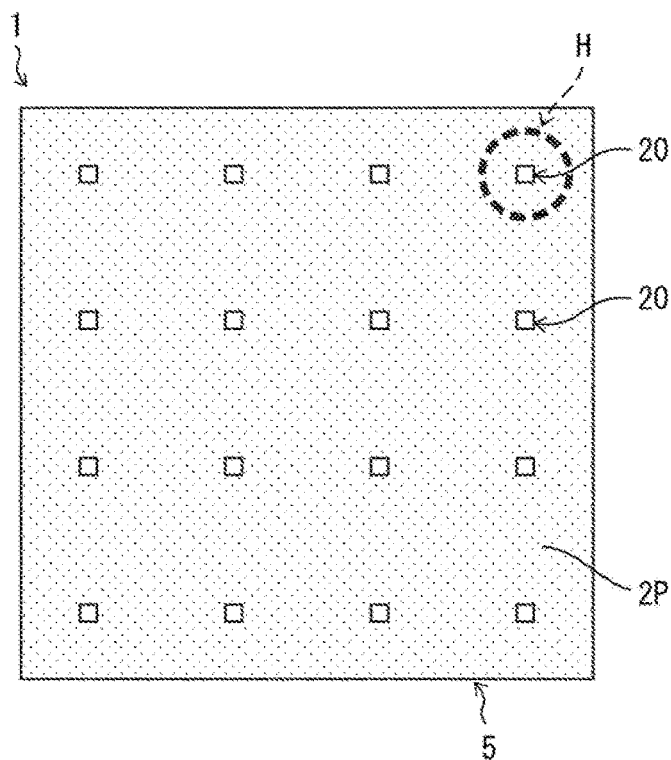
FIG. 1 is a front view schematically illustrating a configuration of a front side of an irradiation substrate 1 in accordance with Embodiment 1.
Figure 2:
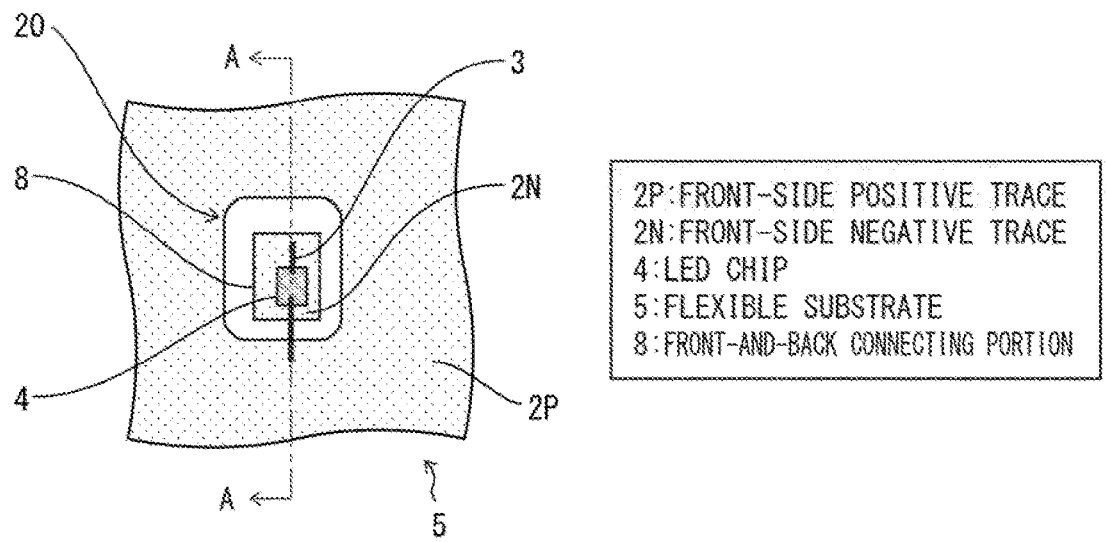
FIG. 2 is an enlarged front view schematically illustrating a configuration of an LED chip placement area enclosed by circle H in FIG. 1.
Figure 3:
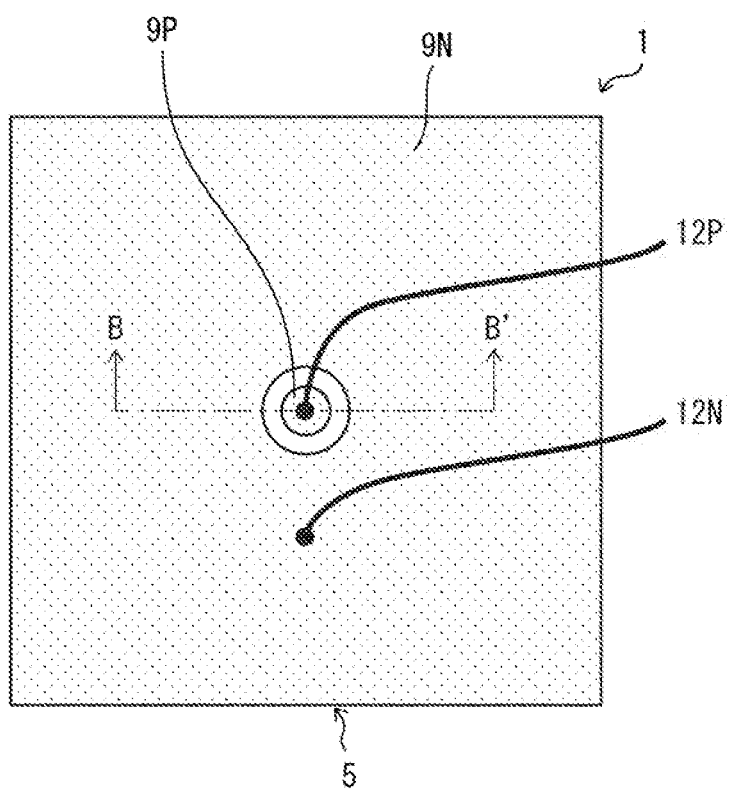
FIG. 3 is a backside perspective view schematically illustrating a configuration of a back side of the irradiation substrate.
Figure 4:
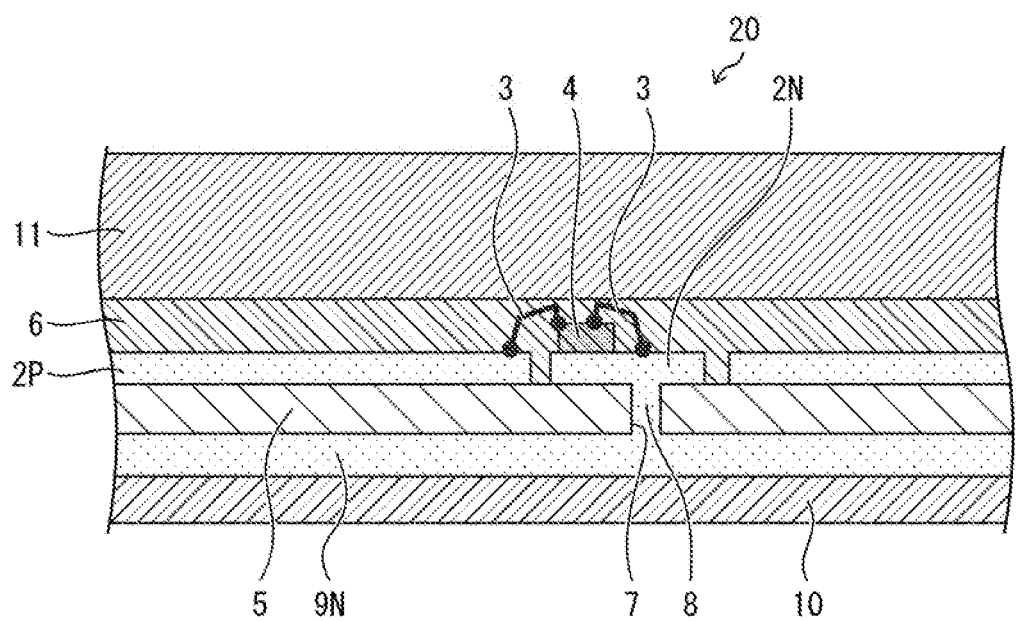
FIG. 4 is a cross-sectional view schematically illustrating a configuration along plane AA shown in FIG. 2.
Figure 5:
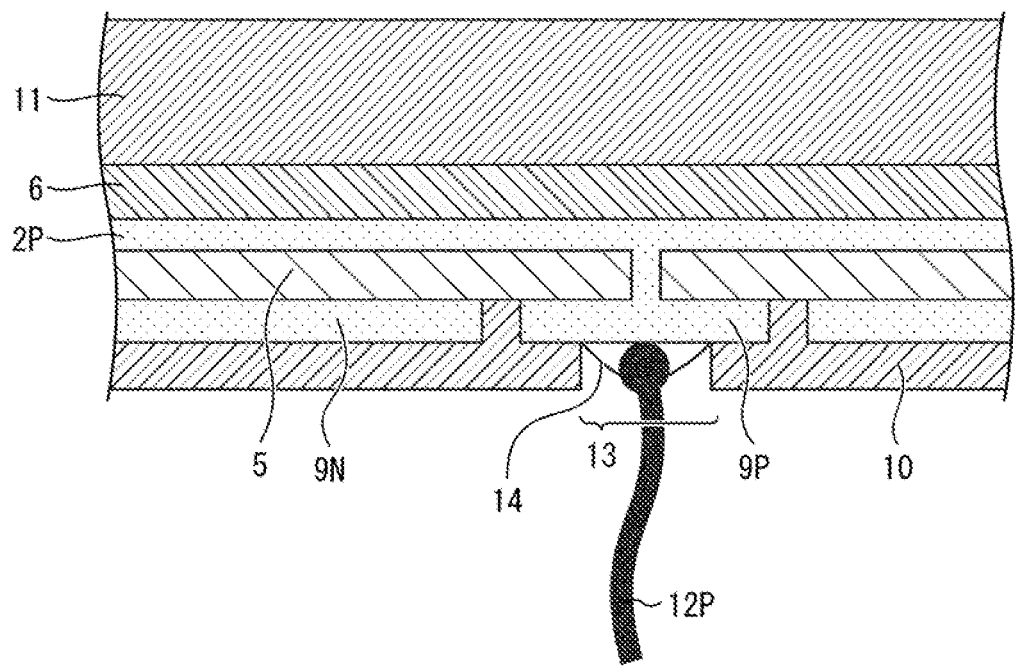
FIG. 5 is a cross-sectional view schematically illustrating a configuration along plane BB shown in FIG. 3.

FIG. 1 is a front view schematically illustrating a configuration of a front side of an irradiation substrate 1 in accordance with Embodiment 1. FIG. 2 is an enlarged front view schematically illustrating a configuration of an LED chip placement area 20 enclosed by circle H in FIG. 1. FIG. 3 is a backside perspective view schematically illustrating a configuration of a back side the irradiation substrate 1. FIG. 4 is a cross-sectional view schematically illustrating a configuration along plane AA shown in FIG. 2. FIG. 5 is a cross-sectional view schematically illustrating a configuration along plane BB shown in FIG. 3.

(Configuration of Irradiation Substrate 1)

The irradiation substrate 1 includes a flexible substrate 5. The flexible substrate 5 has, on the front side thereof, an array of sixteen LED chip placement areas 20 arranged in 4 rows×4 columns. The flexible substrate 5 further has a front-side positive trace 2P (trace, front-side trace part, allover trace) disposed on the entire area of the front side of the flexible substrate 5 such that each LED chip placement area 20 is surrounded by the front-side positive trace 2P.

For convenience of description, this specification is based on the assumption that the front-side positive trace 2P connected to a positive electrode of each LED chip 4 is mainly disposed on the front side of the flexible substrate 5 whereas a back-side negative trace 9N connected to a negative electrode of each LED chip 4 is mainly disposed on the back side of the flexible substrate 5; however, it should be understood that an arrangement obtained by swapping positive and negative is also available similarly.

As illustrated in FIG. 4, each LED chip placement area 20 has a connecting hole 7 in the middle thereof, which passes through the flexible substrate 5. A front-side negative trace 2N (trace, front-side trace part, allover trace) is disposed on the front side of the flexible substrate 5 separately from the front-side positive trace 2P so as to cover the connecting hole 7.

On each front-side negative trace 2N, a light emitting diode chip (hereinafter referred to as an LED chip) 4 serving as a light source is mounted. A bonding wire 3 electrically connects the LED chip 4 and the front-side positive trace 2P, and another bonding wire 3 electrically connects the LED chip 4 and the front-side negative trace 2N, as illustrated in FIG. 4.

The flexible substrate 5 has a connecting hole at the center thereof, as illustrated in FIG. 5. On the back side of the flexible substrate 5, a back-side positive trace 9P, which covers the connecting hole, is disposed so as to connect to the front-side positive trace 2P through the connecting hole. On the back side of the flexible substrate 5, the back-side negative trace 9N (trace, back-side trace part, allover trace) is disposed all over the surface so as to surround the back-side positive trace 9P.

Each front-side negative trace 2N is connected to the back-side negative trace 9N via a front-and-back connecting portion 8 (trace) residing in the connecting hole 7, as illustrated in FIG. 4.

The back-side positive trace 9P is connected with a positive external connection line 12P (electric power supply part) with a solder 14. The positive external connection line 12P is used to externally supply electric power. The back-side negative trace 9N has a negative external connection line 12N (electric power supply part) connected at the center thereof with a solder. The negative external connection line 12N is used to externally supply electric power.

The flexible substrate 5 has a front side protective film 6 disposed all over the front surface thereof such that the front side protective film 6 covers the front-side positive trace 2P, the front-side negative traces 2N, the LED chips 4, and the bonding wires 3.

The flexible substrate 5 has a back side protective film 10 disposed on the back side thereof such that the back side protective film 10 covers the back-side negative trace 9N. The back side protective film 10 has an opening 13, in which a point where the positive external connection line 12P and the back-side positive trace 9P are connected together is exposed.

The flexible substrate 5's surface bearing the LED chips 4 serves as a light emitting surface. The flexible substrate 5 is positioned such that the light emitting surface faces a treatment target area, and thereby light is applied to the treatment target area. The flexible substrate 5 has, on its light-emitting-surface side, a spacer 11 for maintaining an appropriate distance between the treatment target area and the LED chips 4.

Figure 6:
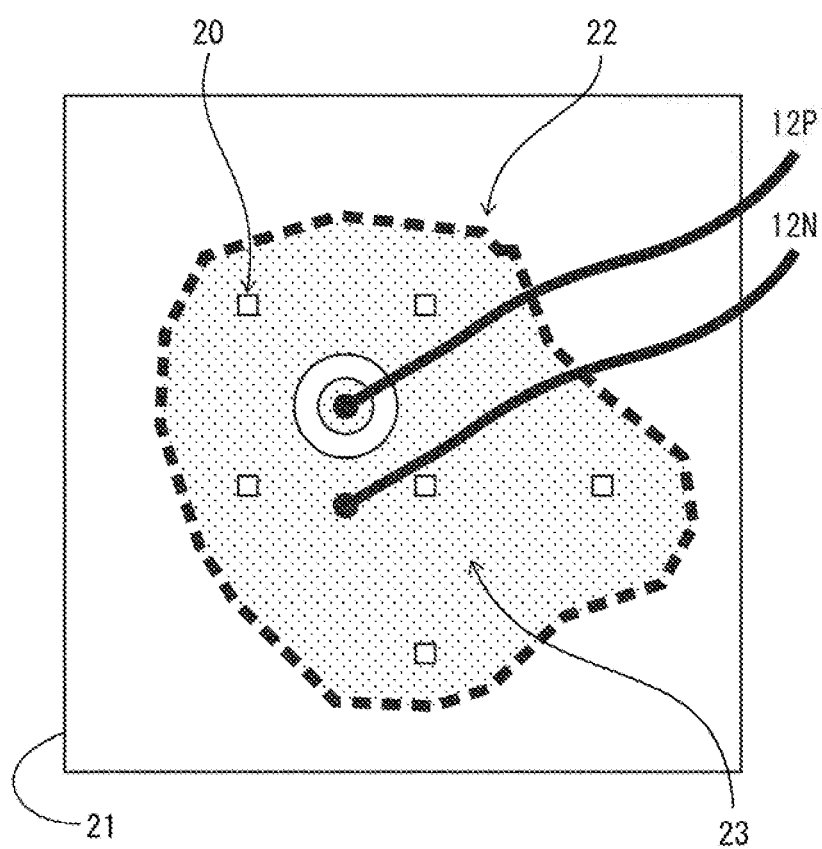
FIG. 6 is a schematic front view for explaining a method of carrying out treatment with the use of the irradiation substrate.

FIG. 6 is a schematic front view for explaining a method of carrying out treatment with the use of the irradiation substrate 1. In phototherapy, treatment target areas of various shapes, sizes, and areas are treated. Therefore, in some kinds of treatment, it is preferable to apply light only to a treatment target area where possible. For example, in a case of treating alopecia areata, it would be preferable if there is an irradiation substrate that only covers a hairless part. A conventional large-size irradiation substrate inevitably covers also a haired area, and the hairless part and the irradiation substrate poorly fit each other. This results in a reduction of effects of irradiation, and also in possible adverse effects on the haired area. Furthermore, in treating a decubitus ulcer, covering an area including a normal skin portion with an irradiation substrate may result in an extension of the decubitus ulcer toward the normal skin portion. Furthermore, in treating periodontoclasia, it is preferable to apply light only to a tooth of interest.

Under such circumstances, there is a demand for an irradiation substrate that can be processed into an appropriate size suitable for the size of a treatment target area at a site where treatment is carried out.

Referring to FIG. 6, the irradiation substrate 1 can be cut into a piece of any shape centered on a position connected to the negative external connection line 12N and the positive external connection line 12P, and irradiation can be carried out with the use of the cut piece. FIG. 6 illustrates one example of the shape of the cut piece. By preparing an irradiation substrate 23 that has been cut to match the shape and size of a treatment target area 22 of a skin 21, it is possible to apply light only to the treatment target area 22 with the use of the irradiation substrate 23.

(Flexible Substrate 5, Front-Side Positive Trace 2P, and Front-Side Negative Trace 2N)

The flexible substrate 5 is constituted by an insulative film such as a polyimide film. Note, however, that the material for the flexible substrate 5 is not limited to polyimide, and may be any material provided that the material has an insulating property and necessary levels of strength and flexibility. The material for the flexible substrate 5 may be transparent or opaque.

The flexible substrate 5 is preferably much thicker than trace materials such as the front-side positive trace 2P, and is required to be thick without dramatically impairing cuttability, as will be described later. In Embodiment 1, the flexible substrate 5 is a polyimide film 50 µm in thickness.

On the front and back surfaces of the flexible substrate 5, copper thin films each 3 µm in thickness are formed, which are then processed into (i) the front-side positive trace 2P and the front-side negative traces 2N and (ii) the back-side positive trace 9P and the back-side negative trace 9N. The connecting holes 7 and the front-and-back connecting portions 8 can be formed by a known technique, and traces such as the front-side positive trace 2P and the back-side negative trace 9N on the front and back sides can be formed by a known technique. If the traces such as the front-side positive trace 2P and the back-side negative trace 9N are thicker than the flexible substrate 5, deformed cut faces may result when the substrate is cut, which may cause the traces on the front and back sides to make contact with each other. By ensuring that the flexible substrate 5 is sufficiently thicker than the traces, it is possible to prevent operation failures that would be caused by such an electrical short-circuit. In a case where a polyimide film was 50 µm in thickness and traces were each 25 µm in thickness, about 50% substrates suffered a short-circuit defect resulting from cutting. On the other hand, in a case were traces were each 10 µm in thickness, the short-circuit defect dramatically reduced to about 1%. Furthermore, in a case where traces were each 3 µm in thickness, no short-circuit defects were found, as far as tested.

The internal stress of a thin film constituting each trace is preferably tensile (tensile stress). This is because such a thin film shrinks a little when cut and the cut face of the thin film withdraws backward, reducing the likelihood of short circuiting. A thin film in which the internal stress is compressive (compressive stress) causes the opposite phenomenon and thus is not preferred.

The surfaces of the front-side positive trace 2P, the front-side negative traces 2N, and the front-and-back connecting portions 8 of the flexible substrate 5 are preferably covered with a silver coating layer. This is to direct maximum possible amounts of (i) light output from the LED chips 4 and reflected at the front-side positive trace 2P on the front side of the substrate and (ii) light output from the LED chips 4 and reflected from the treatment target area to the treatment target area to thereby minimize loss of light. Without the silver coating layer, copper traces absorbed light and the duration of light application to the treatment target area increased 1.2 times in some cases. Other materials with low electric resistance and high reflectivity include aluminum materials and aluminum alloy materials, each of which can be used in place of the silver coating layer. In a case where the emission wavelength of the LED chips 4 is that of red light or infrared light, a gold thin film can be used as a material for the traces such as the front-side positive trace 2P and the front-side negative traces 2N because gold is highly reflective with respect to such light.

(LED Chip 4)

The LED chips 4 are selected according to the purpose of treatment of a treatment target area to be irradiated. In Embodiment 1, the LED chips 4 are gallium-nitride-based blue-violet LEDs (peak wavelength: 410 nm). Other options are: ultraviolet LEDs, blue LEDs, and green LEDs, which are also gallium nitride (AlInGaN) LEDs; four-component (AlGaInP) red, yellow, and green LEDs; GaAs-based infrared LEDs; and the like, from which most appropriate LEDs can be selected depending on the purpose. The LED chips 4 can be composed of a combination of LEDs of two or more different wavebands.

In order to apply light to a treatment target area of a certain size in a uniform manner in phototherapy, it is more preferable to arrange a large number of relatively low-power LED chips on an irradiation substrate than using a small number of high-power LED chips. In Embodiment 1, sixteen blue-violet LED chips 4 each 440 μm×550 μm in size are mounted on the flexible substrate 5. The LED chips 4 are arranged in an array of 4 rows×4 columns, and the average spacing between the LED chips 4 is about 5 mm. These LED chips 4 are bonded to the front-side negative traces 2N with a transparent die attach paste, and are connected to the front-side positive trace 2P and the front-side negative traces 2N by gold bonding wires 3. The bonding wires 3 are not limited to gold, and may alternatively be silver or aluminum.

In a case where four-component (AlGaInP) LEDs or GaAs infrared LEDs are used for treatment, connections are made in the following manner: since these LED chips 4 have a so-called vertical structure, the substrate-side of each LED chip 4 is bonded to the front-side negative trace 2N with a conductive material such as a silver paste and the upper electrode and another trace are connected together by a bonding wire 3. Alternatively, each LED chip 4 may be connected to the front-side positive trace 2P and the front-side negative trace 2N through flip chip attachment by bridging the front-side positive trace 2P and the front-side negative trace 2N. An LED device, which includes a package and the LED chips 4 housed therein, may be used. In a case where the LED device is used, the LED device is solder connected to the front-side positive trace 2P and the front-side negative trace 2N by bridging the front-side positive trace 2P and the front-side negative trace 2N.

In order to make the irradiation intensity of the irradiation substrate 1 as uniform as possible, one option is to pass substantially equal amounts of electric current through the LED chips 4. In Embodiment 1, the front and back surfaces of the flexible substrate 5 are almost entirely covered by positive and negative traces (front-side positive trace 2P and front-side negative traces 2N) as illustrated in FIGS. 1 and 3, and thereby the electric resistance from the center, which is connected to the positive external connection line 12P and the negative external connection line 12N, of the flexible substrate 5 to a peripheral portion of the flexible substrate 5 is reduced.

However, shorter trace distances will result in lower electric resistances. Therefore, there is still a tendency that the amounts of electric current passing through LED chips 4 near the point connected to the positive external connection line 12P are larger than the amounts of electric current passing through LED chips 4 in the peripheral portion of the flexible substrate 5. This causes a concern that the amounts of electric current passing through the LED chips 4 near the above connection point and the amounts of electric current passing through the LED chips 4 in the peripheral portion of the flexible substrate 5 are different from each other and that the emission intensity of the irradiation substrate 1 becomes non-uniform.

However, in reality, in Embodiment 1, a difference in light intensity between the LED chips 4 near the periphery of the flexible substrate 5 and the LED chips 4 near the center of the flexible substrate 5 was not greater than 5%, and no significant non-uniformity was observed.

Figure 7:
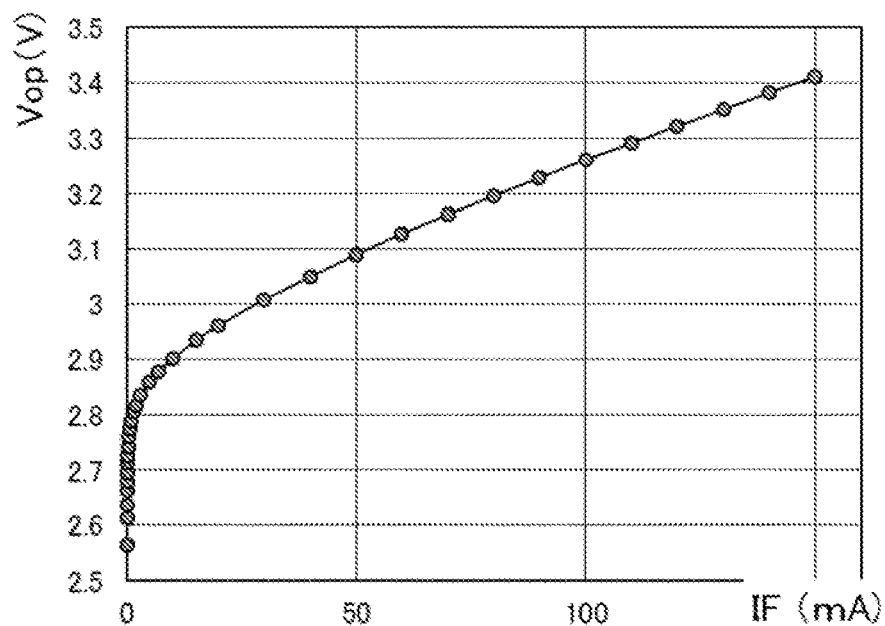
FIG. 7 is a graph showing typical current-voltage characteristics of an LED chip included in the irradiation substrate.
Figure 8:
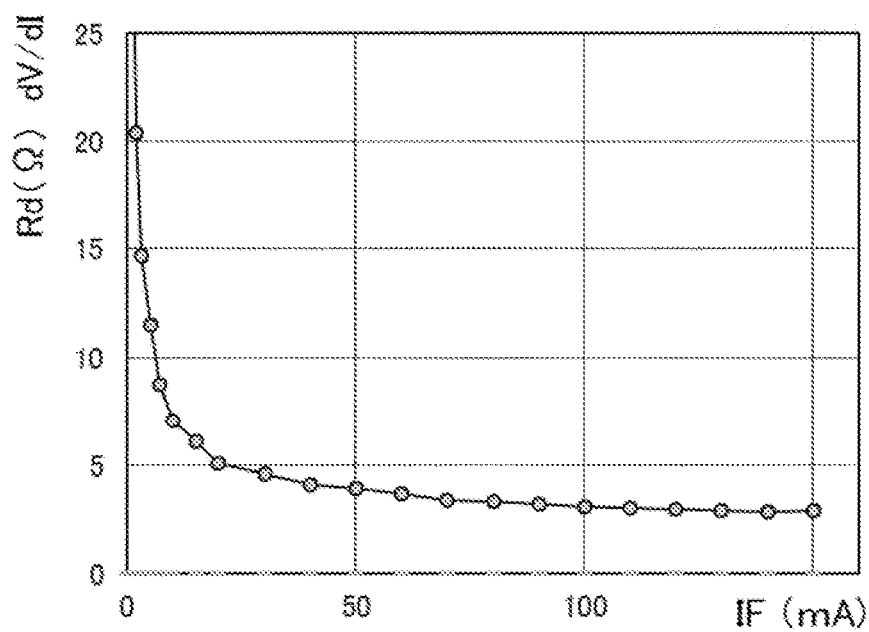
FIG. 8 is a graph showing typical differential resistance characteristics of the LED chip.

This can be explained as below. FIG. 7 is a graph showing typical current-voltage characteristics of an LED chip 4 included in the irradiation substrate 1. FIG. 8 is a graph showing typical differential resistance characteristics of the LED chip 4.

The internal series resistance of each LED chip 4 of Embodiment 1 is found to be about 3Ω from FIGS. 7 and 8. The resistance of the front-side positive trace 2P and the back-side negative trace 9N between adjacent LED chips 4 is about 0.05Ω to 0.1Ω, and therefore, assuming that an electric current of about 100 mA is passed through each LED chip 4, there is a potential difference of about 0.005 V to 0.01 V between adjacent LED chips 4. This means that there will be a difference in electric current of 1.7 mA to 3.3 mA between adjacent LED chips 4. Specifically, one of two adjacent LED chips 4 which is nearer the periphery experiences an electric current reduction of about 1.7% to 3.3% as compared to the other of the LED chips 4 which is nearer the center. Since the emission intensity of each LED chip 4 is substantially proportional to the electric current value, the difference in emission intensity between LED chips 4 is also about 1.7% to 3.3%, which is not greater than 5%. The electric resistance between [an LED chip 4 in the peripheral portion of the flexible substrate 5] and [the positive external connection line 12P and the negative external connection line 12N (electric power supply part)] is not limited, provided that the electric resistance is less than the internal resistance of that LED chip 4. The electric resistance is preferably not greater than one-tenth of the internal resistance, more preferably not greater than one-thirtieth of the internal resistance. The electric resistance between the electric power supply part and the LED chip 4 as used herein refers to, more precisely, the sum of the electric resistance from the positive external connection line 12P to the LED chip 4 and the electric resistance from the LED chip 4 to the negative external connection line 12N; however, the resistances of the positive external connection line 12P and the negative external connection line 12N, and the resistances of the points connected to the positive external connection line 12P and the negative external connection line 12N, are usually small, and therefore the electric resistance between the electric power supply part and the LED chip 4 can be represented substantially by the sum of the electric resistance from the back-side central positive trace 9P to the LED chip 4 and the electric resistance from the LED chip 4 to a portion of the back-side negative trace 12N which is in contact with the negative external connection line 12N. The portion of the back-side negative trace 12N which is in contact with the negative external connection line 12N herein usually refers to a portion nearest the back-side central positive trace 9P.

In regard to the internal resistance of each LED chip 4, it is inferred that variations in internal resistance among a plurality of LED chips 4 are very small, and therefore the foregoing description does not specify which LED chip 4 has the foregoing internal resistance. However, in a case where it should be made clear about which LED chip 4 has the foregoing internal resistance, then it is assumed here that the foregoing internal resistance is that of the LED chip 4 farthest from the electric power supply part. This is because understanding becomes easier when the trace resistance and the internal resistance are compared to each other for the same LED chip 4. The same applies to the other embodiments.

In Embodiment 1, each of the LED chip placement areas 20 includes one LED chip 4, and all the LED chip placement areas 20 are connected in parallel to the electric power supply part. With this arrangement, the irradiation substrate 1 can be cut into any shape, as described earlier. Furthermore, the LED chips 4 can be driven with a low voltage of not higher than 5 V, and therefore can be easily driven by a battery or a storage battery. Alternatively, a plurality of LED chips 4 can be placed in a single LED chip placement area 20. For example, an LED chip that emits blue-violet light and an LED chip that emits red light can be connected in series and placed in a single LED chip placement area 20. Also in this case, the LED chips can be driven with a voltage of about 6 V, and also can be easily driven by a battery or a storage battery. Alternatively, a plurality of LEDs that emit the same color of light, connected in series or parallel to each other, can be placed in a single LED chip placement area 20.

(Front Surface Protective Film 6, Back Side Protective Film 10, Spacer 11)

The front side protective film 6, which is made of a silicone resin, is disposed all over the front surface of the flexible substrate 5 to protect the LED chips 4, bonding wires 3, front-side positive trace 2P, and front-side negative traces 2N. The front side protective film 6 serves not only to prevent short-circuits between the front-side positive trace 2P and the front-side negative traces 2N, but also to prevent the corrosion of the front-side positive trace 2P and the front-side negative traces 2N.

When irradiation is carried out, one option that can be used to maintain the separation between the flexible substrate 5 and the treatment target area is the spacer 11. The spacer 11 can be any of various types, including: a resin material such as a polystyrene elastomer, a polyurethane resin, or a silicone rubber, each having a certain thickness (e.g., 5 mm in thickness); a plastic bag processed to maintain a certain thickness that is filled with water or air; a water absorptive polymer processed into a sheet with a certain thickness; and the like. A transparent material containing a scatterer makes it possible to achieve a spacer 11 that is thinner but achieves more uniform light intensity. In a case where the spacer 11 is made of an insulative resin material, the front side protective film 6 and the spacer 11 can be formed integrally with each other. The spacer 11 also serves as a heat insulator that prevents the treatment target area from being heated by head generated by the LED chips 4.

The spacer 11 may be attached to the front surface of the irradiation substrate 1 beforehand, or may be placed on a treatment target area and then attached to the irradiation substrate 1 when irradiation is to be carried out. In the former case, the operation of attaching the irradiation substrate 1 to the treatment target area can be simplified. The latter case is advantageous in that, although the processing of the spacer 11 and the processing of the irradiation substrate 1 are carried out separately, each of the processing operations is easy.

In irradiating a treatment target area with uniform intensity, a relationship between a thickness T of the spacer 11 and an average distance D between LED chips 4 plays an important role. In a case where the spacer 11 does not contain any scatterer, the thickness T and the average distance D should at least satisfy $0.5 \leq T/D$, preferably $0.8 \leq T/D$. If the value of T/D is less than 0.5, the irradiation intensity at a position on the surface of the treatment target area right below an LED chip 4 is about twice as large as the irradiation intensity at a position on the surface of the treatment target area right below the middle of two adjacent LED chips 4. This means that the irradiation intensity is significantly non-uniform and is thus not preferred.

The irradiation substrate 1 can include a temperature sensor, a light intensity sensor, and/or the like and thereby monitor temperature and/or light intensity.

(Positive External Connection Line 12P, Negative External Connection Line 12N, Back-Side Negative Trace 9N, Back-Side Positive Trace 9P)

In Embodiment 1, as illustrated in FIG. 3, the positive external connection line 12P and the negative external connection line 12N are run from the backside of the flexible substrate 5. The back-side positive trace 9P is linked to the front-side positive trace 2P via the connecting hole. The positive external connection line 12P and the negative external connection line 12N are lines to be connected to an electric power source that supplies electric current to the irradiation substrate 1. The lines are preferably terminated with a socket, a plug, or the like to be easily connected to the electric power source, for more convenient connection with the electric power source. The negative external connection line 12N and the positive external connection line 12P are connected to the back-side negative trace 9N and the back-side positive trace 9P, respectively, with the solder 14.

FIG. 5 illustrates an arrangement in which the back side protective film 10 is formed, the opening 13 is formed in the back side protective film 10, and the positive external connection line 12P is connected to the back-side positive trace 9; however, the present invention is not limited as such. The following arrangement may be employed: the negative external connection line 12N is provided to the back-side negative trace 9N, the positive external connection line 12P is provided to the back-side positive trace 9P, and then the back side protective film 10 is formed all over the back surface of the flexible substrate 5. This arrangement is advantageous in that connection points are covered and protected by the back side protective film 10. Note that, although FIGS. 3 and 5 schematically illustrate the negative external connection line 12N and the positive external connection line 12P in the form of lead wires, the present invention is not limited as such. This arrangement is merely an example, and the scope of Embodiment 1 also encompasses an arrangement in which the negative external connection line 12N and the positive external connection line 12P are actually connectors or the like disposed on the substrate for connection with lead wires (the same applies to the other embodiments).

(Effect Verification)

In Embodiment 1, an irradiation substrate in accordance with Embodiment 1 was applied to treatment of a skin lesion of methicillin-resistant *Staphylococcus aureus* (MRSA) infection (intractable decubitus ulcer model) formed on the back of each laboratory mouse, and a therapeutic effect was verified. As illustrated in FIG. 6, the irradiation substrate 1 was cut into a shape that matches the shape of a treatment target area 22 of a skin 21 having a size of about 15 mm, thereby obtaining an irradiation substrate 23 having the same shape as the treatment target area but a little larger (about 1 mm) than the treatment target area. Light used for the treatment had a wavelength of 410 nm.

In Embodiment 1, two laboratory mice A and B were prepared, and one of them (mouse A) was irradiated with light with the use of a conventional lamp-type irradiation apparatus, whereas the other of them (mouse B) was irradiated with light with the use of the apparatus of Embodiment 1. Then, how the condition of the treatment target area changed after irradiation with light was checked.

For each of the mice A and B, a 5-aminolevulinic ointment was applied as a therapeutic agent to the treatment target area and, 4 hours after the application of the ointment, light was applied. In regard to the mouse B, the irradiation substrate 23 was fixed to the treatment target area with a bandage, an electric current of 500 mA at 3.3 V was supplied to an external connection part from an external electric power source for 4 minutes, and an energy dose of at least 30 J/cm$^2$ was given to the treatment target area. A cooled cold reserving material was placed on the irradiation substrate 23 for cooling, and thereby the irradiation substrate 23 was cooled. In regard to the mouse A, the same dose of irradiation was carried out with the use of a lamp-type irradiation apparatus.

After the above processes, the treatment target area and its surrounding areas of each of the two mice A and B were checked, and it was found that the conditions of the treatment target areas of both of the mice improved. That is, substantially the same therapeutic effect was obtained. In regard to the mouse A, after the irradiation, a trouble of skin erosion was observed around the treatment target area. On the other hand, in regard to the mouse B, such a trouble was not observed at all.

Embodiment 2

Figure 9:
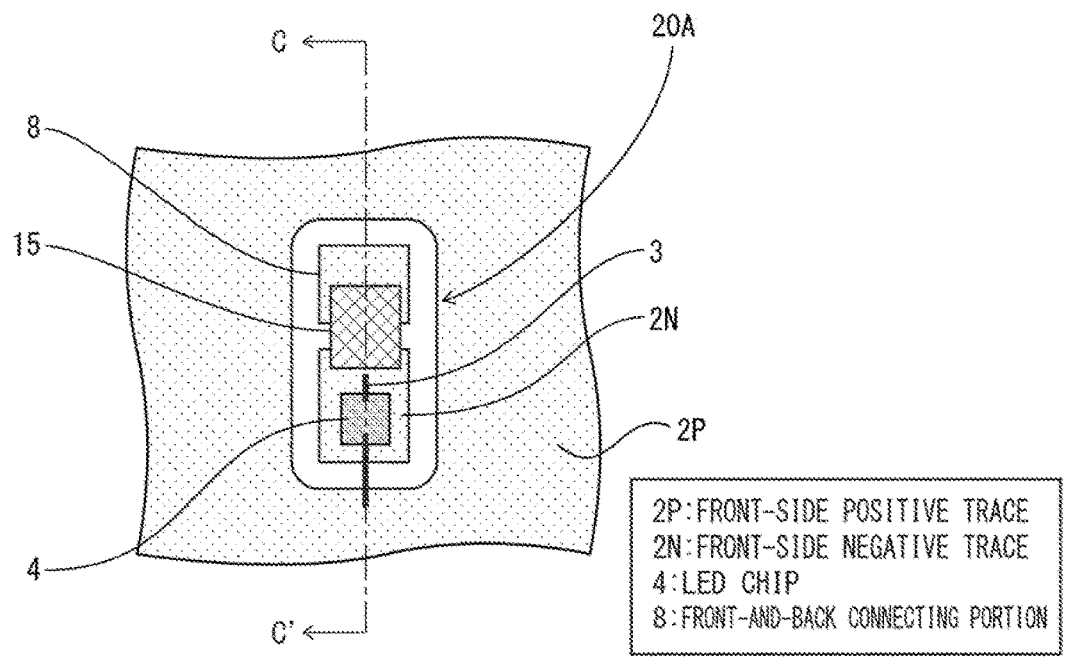
FIG. 9 is an enlarged front view schematically illustrating a configuration of an LED chip placement area of an irradiation substrate in accordance with Embodiment 2.
Figure 10:
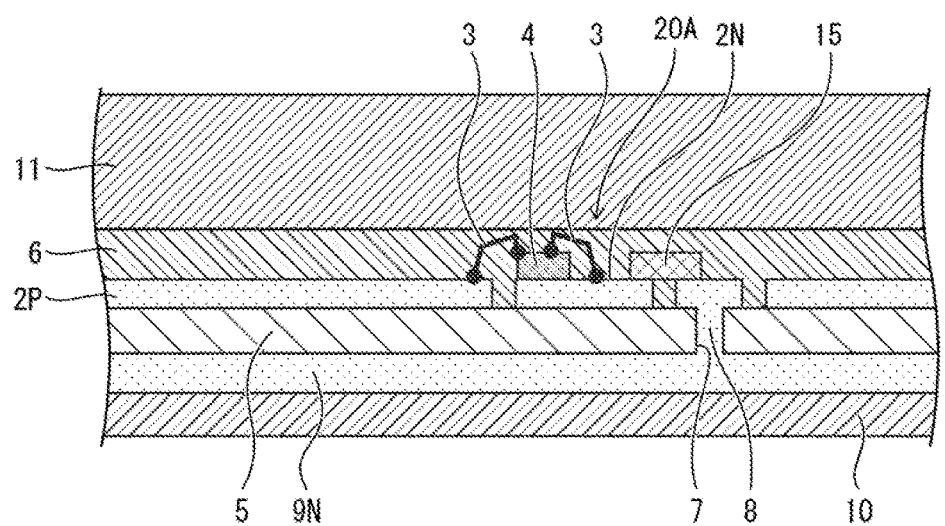
FIG. 10 is a cross-sectional view schematically illustrating a configuration along plane CC shown in FIG. 9.

The following description will discuss another embodiment of the present invention with reference to FIGS. 9 and 10. For convenience of description, members having functions identical to those described in Embodiment 1 are assigned identical referential numerals and their descriptions are omitted.

Embodiment 2 is the same as Embodiment 1, except that a configuration of each LED chip placement area 20A is different.

In Embodiment 1, the flexible substrate 5 has low-electric-resistance traces (front-side positive trace 2 and back-side negative trace 9N) formed on the front and back surfaces thereof, and thereby the internal series resistance of each LED chip 4 is made dominant. This reduces the difference in emission intensity among the LED chips 4 of the irradiation substrate 1.

However, even if all the LED chips 4 emit light of the same intensity, a light intensity at the outer portion (peripheral portion) of the irradiation substrate 1 is inevitably lower than a light intensity at the central portion of the irradiation substrate 1, because, at the central portion of the irradiation substrate 1, not only light from LED chips 4 in the central portion but also light from LED chips 4 in the outer portion (peripheral portion) contributes to the light intensity, whereas, in the outer portion (peripheral portion) of the irradiation substrate 1, there are no LED chips 4 outside the peripheral portion. Therefore, with the irradiation substrate 1 in accordance with Embodiment 1, in order to achieve a desired therapeutic effect using an irradiation substrate having the same size and shape as a treatment target area, it is necessary to make irradiation time longer to compensate for the lower light intensity at the outer portion (peripheral portion) than the light intensity at the central portion. Embodiment 2 is to shorten the treatment time by reducing the aforementioned in-plane variations in light intensity of the irradiation substrate 1, that is, by causing the emission intensity of the LED chips 4 in the outer portion (peripheral portion) to be greater than the emission intensity of the LED chips 4 in the central portion.

FIG. 9 is an enlarged front view schematically illustrating a configuration of an LED chip placement area 20A of an irradiation substrate in accordance with Embodiment 2. FIG. 10 is a cross-sectional view schematically illustrating a configuration along plane CC shown in FIG. 9.

As illustrated in FIGS. 9 and 10, in Embodiment 2, a chip resistor 15 is mounted between the front-side negative trace 2N and the front-and-back connecting portion 8. The chip resistor 15 has an electric resistance value greater than that of the LED chip 4, front-side positive trace 2P, back-side negative trace 9N, and the like. By selecting an appropriate electric resistance value for the chip resistor 15, it is possible to control electric current passing through each LED chip 4.

In Embodiment 2, LED chip placement areas 20A in the peripheral portion of the flexible substrate 5 are provided with no chip resistor 15 (chip resistor value=0), that is, the front-side negative trace 2N and the front-and-back connecting portion 8 are short-circuited. On the other hand, LED chip placement areas 20A in the inner portion of the flexible substrate 5 are provided with a chip resistor of 3.5Ω.

This achieved the following. In a case where no chip resistors 15 were added to the LED chip placement areas 20A in the inner portion, the light intensity at the LED chip placement areas 20A in the peripheral portion of the flexible substrate 5 was about 50% that at the LED chip placement areas 20A in the inner portion; however, in a case where the chip resistor 15 was added to each of these LED chip placement areas 20A in the inner portion, the percentage of the light intensity of the LED chips 4 in the peripheral portion relative to the light intensity of the LED chips 4 in the inner portion improved to about 80%. This is because the series resistance of each of the LED chips 4 in the inner portion substantially doubled and electric current passing through the LED chips 4 in the inner portion became substantially half of that of the LED chips 4 in the peripheral portion, and thereby the emission intensity of the LED chips 4 in the peripheral portion became much greater than that of the LED chips 4 in the inner portion. It is inferred that, under the conditions in which an electric current of 100 mA passes through the LED chips 4 in the peripheral portion, an electric current of about 50 mA passes through the LED chips 4 in the inner portion because the chip resistor 15 causes a voltage drop and this results in a lowering of applied voltage by about 0.17 V.

Note, however, that, although in-plane uniformity of the irradiation intensity of the irradiation substrate improved, the treatment time cannot be shortened with the use of the same electric current as that of Embodiment 1. This is because the above uniformity is achieved not by increasing the light intensity of the LED chips 4 in the peripheral portion of the flexible substrate 5. Therefore, in order to shorten treatment time, one option is to increase driving electric current and provide larger electric power. This necessitates enhancement of a cooling means, such as placing a cold reserving material on the irradiation substrate 1.

It was verified that the arrangement of Embodiment 2 provides the same effects as those of Embodiment 1.

Embodiment 3

Figure 11:
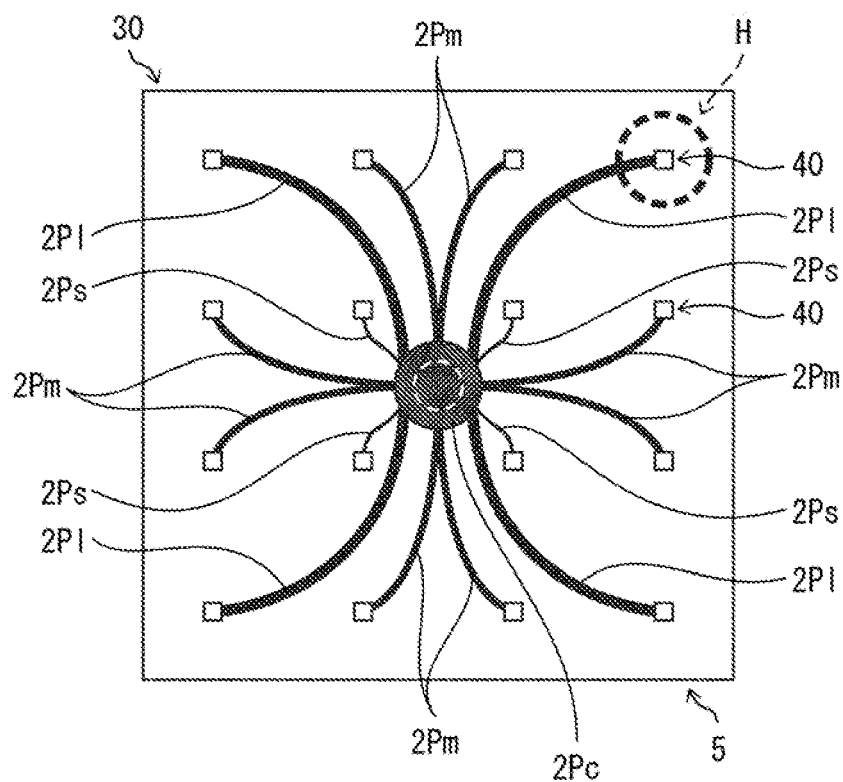
FIG. 11 is a front view schematically illustrating a configuration of an irradiation substrate in accordance with Embodiment 3.

FIG. 11 is a front view schematically illustrating a configuration of an irradiation substrate 30 in accordance with Embodiment 3. The irradiation substrate 30 is the same as the irradiation substrate 1 in accordance with Embodiment 1 in that LED chip placement areas 40 are arranged in an array on the front side of a flexible substrate 5. Embodiment 3 is different from Embodiment 1 in terms of the arrangement of traces connected to LED chips and a material constituting the substrate. Specifically, in Embodiment 3, as illustrated in FIG. 11, the LED chip placement areas 40, in each of which an LED chip is placed, are connected to the center of the flexible substrate 5 via respective different traces.

Each of four LED chip placement areas 40 in the inner portion of the flexible substrate 5 is connected to a front-side central positive trace 2Pc at the center of the flexible substrate 5 by a front-side positive trace 2Ps. Each of eight of twelve LED chip placement areas 40 in the peripheral portion of the flexible substrate 5 except four LED chip placement areas 40 at four corners is connected to the front-side central positive trace 2Pc at the center of the flexible substrate 5 by a front-side positive trace 2Pm. Each of the four LED chip placement areas 40 at the four corners is connected to the front-side central positive trace 2Pc at the center of the flexible substrate 5 by a front-side positive trace 2Pl.

Figure 12:
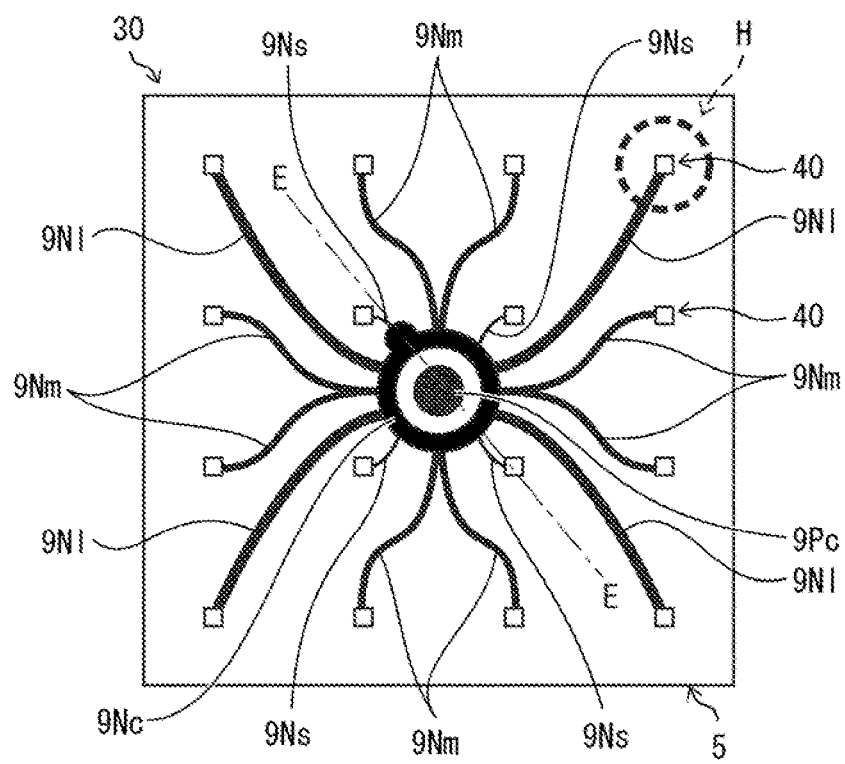
FIG. 12 is a backside perspective view schematically illustrating the configuration of the irradiation substrate.

FIG. 12 is a backside perspective view schematically illustrating the configuration of the irradiation substrate 30. Similarly to the front side illustrated in FIG. 11, also on the back side of the flexible substrate 5, the LED chip placement areas 40, in each of which an LED chip is placed, are connected to the center of the flexible substrate 5 via respective different traces.

Each of four LED chip placement areas 40 in the inner portion of the flexible substrate 5 is connected to a back-side central negative trace 9Nc in annular form at the center of the flexible substrate 5 by a back-side negative trace 9Ns. Each of eight of twelve LED chip placement areas 40 in the peripheral portion of the flexible substrate 5 except four LED chip placement areas 40 at four corners is connected to the back-side central negative trace 9Nc at the center of the flexible substrate 5 by a back-side negative trace 9Nm. Each of the four LED chip placement areas 40 at the four corners is connected to the back-side central negative trace 9Nc at the center of the flexible substrate 5 by a back-side negative trace 9Nl. In a space defined by the inner circumference of the annular back-side central negative trace 9Nc at the center of the flexible substrate 5, there is a back-side central positive trace 9Pc, which is connected to the front-side central positive trace 2Pc.

In order to avoid short-circuits between the front-side positive traces 2Ps and the back-side negative traces 9Ns of the flexible substrate 5, short-circuits between the front-side positive traces 2Pm and the back-side negative traces 9Nm of the flexible substrate 5, and short-circuits between the front-side positive traces 2Pl and the back-side negative traces 9Nl of the flexible substrate 5 when cutting the substrate into a shape that matches a treatment target area as explained earlier with reference to FIG. 6, these traces are arranged such that: the front-side positive traces 2Ps and the back-side negative traces 9Ns do not overlap each other when seen from a direction perpendicular to the flexible substrate 5; the front-side positive traces 2Pm and the back-side negative traces 9Nm do not overlap each other when seen from the direction perpendicular to the flexible substrate 5; and the front-side positive traces 2Pl and the back-side negative traces 9Nl do not overlap each other when seen from the direction perpendicular to the flexible substrate 5.

Since the LED chip placement areas 40 are connected to the center of the flexible substrate 5 via respective different traces as described above, the flexible substrate 5 has a larger exposed area than an arrangement in which the front-side positive trace 2P almost entirely covers the flexible substrate 5 like that described earlier with reference to FIGS. 1 and 2. This increases the area of the front surface of the flexible substrate 5 which reflects light coming from the LED chips 4. Therefore, it is preferable to increase the flexible substrate 5's own reflectivity. Note that, for easy comparison, the backside view in FIG. 12 illustrates the LED chip placement areas 40 as seen through the back surface.

When the length and width of each of the front-side positive traces 2Ps, 2Pm, and 2Pl are controlled and the length and width of each of the back-side negative traces 9Ns, 9Nm, and 9Nl are controlled, the electric resistance value from the center of the flexible substrate 5 to each LED chip placement area 40 is controlled.

As such, on each of the front and back sides of the flexible substrate 5, the LED chip placement areas 40 are provided with respective different traces.

Figure 13:
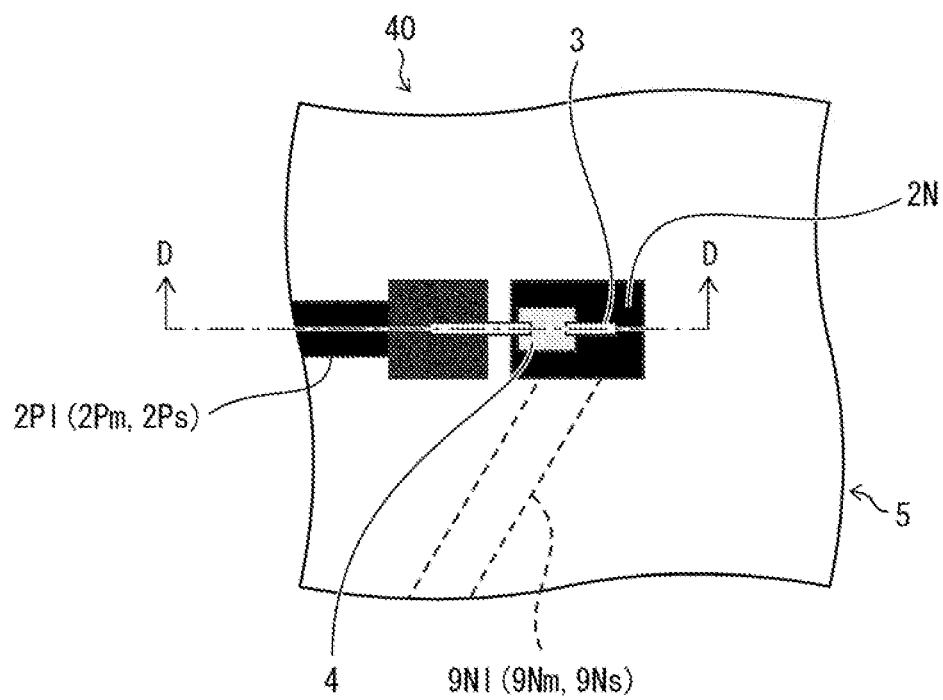
FIG. 13 is an enlarged front view schematically illustrating a configuration of an LED chip placement area enclosed by circle H in FIGS. 11 and 12.
Figure 14:
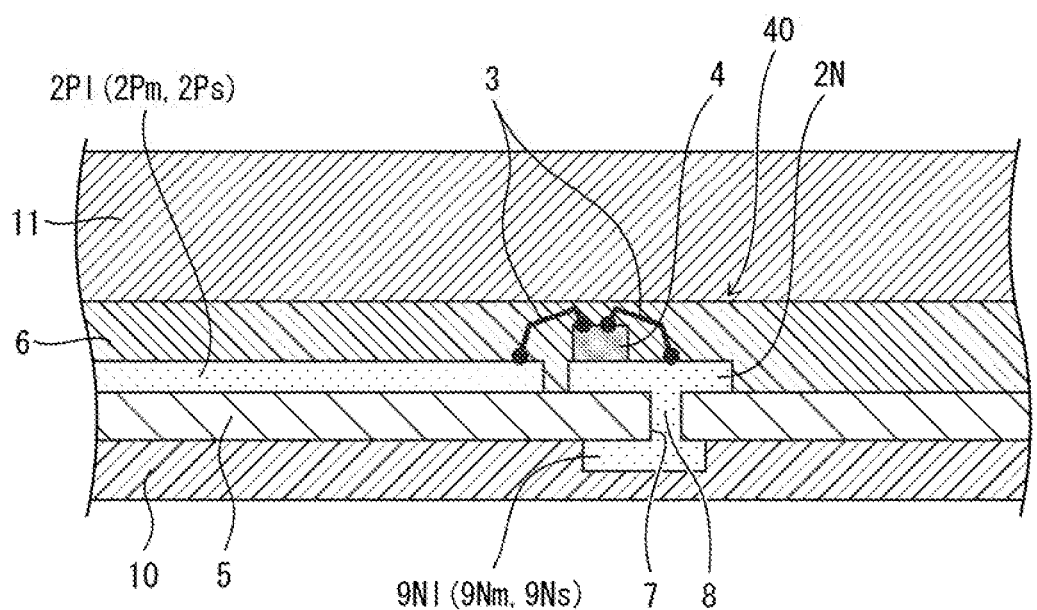
FIG. 14 is a cross-sectional view schematically illustrating a configuration along plane DD shown in FIG. 13.

FIG. 13 is an enlarged front view schematically illustrating a configuration of an LED chip placement area 40 enclosed by circle H in FIGS. 11 and 12. FIG. 14 is a cross-sectional view schematically illustrating a configuration along plane DD shown in FIG. 13. In the LED chip placement area 40, a front-side negative trace 2N is disposed so as to cover a connecting hole 7 in the flexible substrate 5. The front-side positive trace 2Pl (2Pm, 2Ps) extends to a position near the front-side negative trace 2N. An LED chip 4 serving as a light source is mounted on the front-side negative trace 2N. The LED chip 4 and the front-side positive trace 2Pl (2Pm, 2Ps) are connected together by a bonding wire 3, and the LED chip 4 and the front-side negative trace 2N are connected together by another bonding wire 3.

The front-side negative trace 2N is connected to the back-side negative trace 9Nl (9Nm, 9Ns) via a front-and-back connecting portion 8 disposed in the connecting hole 7. The irradiation substrate of Embodiment 3 is the same in structure as that of Embodiment 1, except that the traces are changed as below: the front-side positive trace 2P is replaced by the front-side positive trace 2Pl (2Pm, 2Ps); and the back-side negative trace 9N is replaced by the back-side negative trace 9Nl (9Nm, 9Ns).

Figure 15:
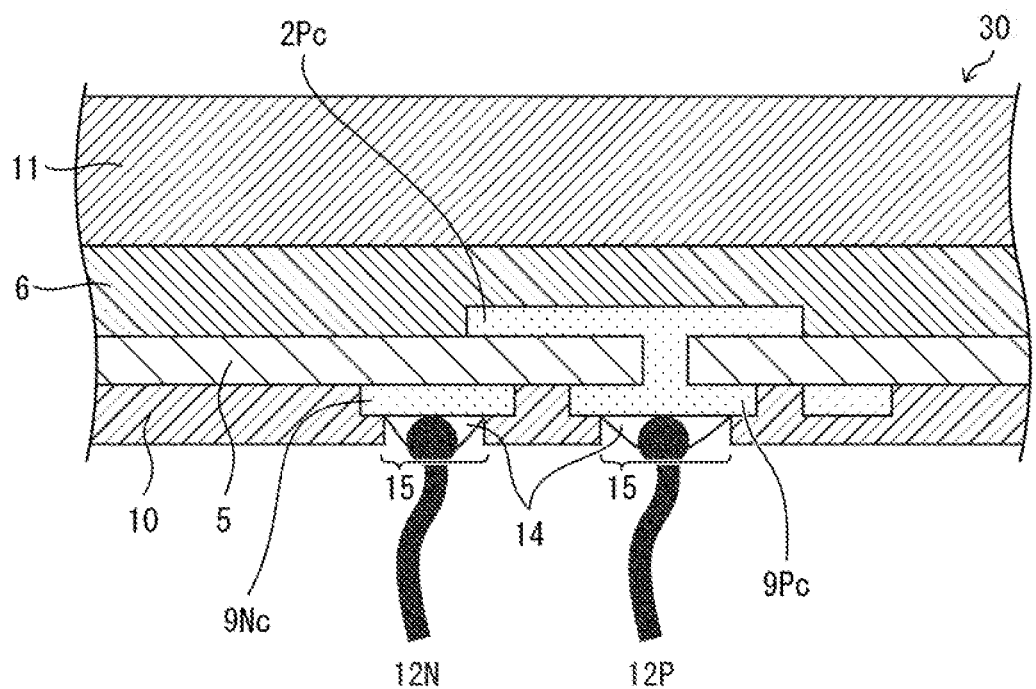
FIG. 15 is a cross-sectional view schematically illustrating a configuration along plane EE shown in FIG. 12.

FIG. 15 is a cross-sectional view schematically illustrating a configuration along plane EE shown in FIG. 12. At the center of the irradiation substrate 30, as illustrated in FIG. 15, the back-side central positive trace 9Pc is disposed which is linked to the front-side central positive trace 2Pc, and a positive external connection line 12P is connected to the back-side central positive trace 9Pc with a solder 14. Similarly, a negative external connection line 12N is connected to the back-side central negative trace 9Nc, which is linked to the back-side negative trace 9Nl (9Nm, 9Ns), with another solder 14. The central portion of the irradiation substrate 30 of Embodiment 3 is the same as that of Embodiment 1, except that the traces are changed as below: the front-side positive trace 2P is replaced by the front-side positive trace 2Pl (2Pm, 2Ps); and the back-side negative trace 9N is replaced by the back-side negative trace 9Nl (9Nm, 9Ns).

(Flexible Substrate 5, Front-Side Positive Trace 2Pl (2Pm, 2Ps), Back-Side Negative Trace 9Nl (9Nm, 9Ns))

A material for the flexible substrate 5 in accordance with Embodiment 3 used here is a material obtained by kneading a white pigment into a silicone resin and forming it into a film form. The thickness of the film is 50 μm. This flexible substrate 5 transmits almost no light and has a high reflectivity of 90% or greater.

On the front and back surfaces of the flexible substrate 5, copper thin films each 10 μm in thickness are formed, and are processed into the front-side positive traces 2Pl (2Pm, 2Ps), front-side central positive trace 2Pc, back-side negative traces 9Nl (9Nm, 9Ns), back-side central positive trace 9Pc, and back-side central negative trace 9Nc. The irradiation substrate of Embodiment 3 is the same as Embodiment 1, except that the copper thin films are thicker than those of Embodiment 1. Since the copper thin films are thicker, there is the likelihood that electrical short-circuit defects will increase when cutting; however, since the traces on the front side and the traces on the back side are routed so as not to overlap each other, no short-circuit defects were observed.

In Embodiment 3, the front-side positive traces 2Pl, the front-side positive traces 2Pm, and the front-side positive traces 2Ps, each of which connects an LED chip placement area 40 and the center of the flexible substrate 5, have substantially equal electric resistance values. The length of each front-side positive trace 2Ps is 2.1 mm, the length of each front-side positive trace 2Pm is 6.1 mm, and the length of each front-side positive trace 2Pl is 9.4 mm. The width of each front-side positive trace 2Ps is 100 μm, the width of each front-side positive trace 2Pm is 290 μm, and the width of each front-side positive trace 2Pl is 448 μm. The front-side positive traces 2Ps, 2Pm, and 2Pl each have an electric resistance value of 0.1Ω. Similarly, the back-side negative traces 9Ns, 9Nm, and 9Nl each have the same electric resistance value of 0.1Ω.

With such an arrangement in which the front-side positive traces 2Ps, 2Pm, and 2Pl and the back-side negative traces 9Ns, 9Nm, and 9Nl each connected to an LED chip placement area 40 have equal electric resistances, the amounts of electric current passing through the LED chips 4 were equal, and thereby the obtained emission intensity was the same among the LED chips 4.

The above description discusses causing the front-side positive traces 2Ps, 2Pm, and 2Pl and the back-side negative traces 9Ns, 9Nm, and 9Nl to have equal electric resistances. This substantially means that the electric resistance from the positive external connection line 12P to an LED chip 4 is the same among different LED chips 4, and the electric resistance from an LED chip 4 to the negative external connection line 12N is the same among different LED chips 4. The resistances of the positive external connection line 12P and the negative external connection line 12N, and the resistances of the points connected to the positive external connection line 12P and the negative external connection line 12N, are usually small, and therefore what should be taken into consideration here are, substantially, only the electric resistance from the back-side central positive trace 9Pc to each LED chip 4 and the resistance from each LED chip 4 to the back-side central negative trace 9Nc. Furthermore, the resistances of the back-side central positive trace 9Pc and the front-side central positive trace 2Pc can usually be reduced sufficiently, and therefore the electric power supply part can be regarded substantially as the front-side central positive trace 2Pc and the back-side central negative trace 9Nc.

(Effect Verification)

In Embodiment 3, an irradiation substrate 30 in accordance with Embodiment 3 was applied to treatment of a lesion of alopecia areata on the back of each laboratory mouse (alopecia areata model mouse (C3H/HeJ mouse)), and a therapeutic effect was verified. As illustrated in FIG. 6 mentioned earlier, the irradiation substrate was cut into a shape that matches the shape of a treatment target area 22 of a skin 21 having a size of about 15 mm, thereby obtaining an irradiation substrate 23 having the same shape as the treatment target area but a little larger (about 1 mm) than the treatment target area. Light used for the treatment, which is emitted from the irradiation substrate 23, had a wavelength of 630 nm.

In Embodiment 3, two mice A and B were prepared, and one of them (mouse A) was irradiated with light with the use of a conventional lamp-type irradiation apparatus and the other of them (mouse B) was irradiated with light with the use of the irradiation substrate 23 of Embodiment 3. Then, how the condition of the treatment target area changed after irradiation with light was checked.

In regard to the mouse B, the irradiation substrate 23 was fixed to the treatment target area with a bandage, an electric current of 500 mA at 2.5 V was supplied to an external connection part (positive external connection line 12P, negative external connection line 12N) from an external electric power source for 5.2 minutes, and an energy dose of at least 30 J/cm$^2$ was given to the treatment target area. A cooled cold reserving material was placed on the irradiation substrate 23 for cooling, and thereby the irradiation substrate 23 was cooled. In regard to the mouse A, the same dose of irradiation as the mouse B was carried out with the use of a lamp-type irradiation apparatus.

After the above processes, the treatment target area and its surrounding areas of each of the two mice A and B were checked, and it was found that the conditions of the treatment target areas of both of the mice improved. That is, substantially the same therapeutic effect was obtained. In regard to the mouse A, after the irradiation, a trouble of skin erosion was observed around the treatment target area. On the other hand, in regard to the mouse B, such a trouble was not observed at all.

Embodiment 4

Embodiment 4 is different from Embodiment 3 in that the electric resistance of each trace (front-side positive traces 2Ps, 2Pm, and 2Pl, and back-side negative traces 9Ns, 9Nm, and 9Nl) differs depending on the distance from the center of the flexible substrate 5 to each LED chip placement area 40.

Similarly to Embodiment 2, smaller amounts of electric current are passed through LED chips 4 near the center of the flexible substrate 5 than electric current passing through LED chips 4 in the peripheral portion of the flexible substrate 5, and thereby uniformity of irradiation intensity over the entire surface of the irradiation substrate is improved.

Specifically, Embodiment 4 is arranged such that: the front-side positive traces 2Ps, 2Pm, and 2Pl have electric resistances of 1.9Ω, 0.313Ω, and 0.1Ω, respectively; and the front-side positive traces 2Ps, 2Pm, and 2Pl have widths of 5.3 μm, 93 μm, and 448 μm, respectively. The lengths of the front-side positive traces 2Ps, 2Pm, and 2Pl are the same as those of Embodiment 3.

The back-side negative traces 9Ns, 9Nm, and 9Nl have the same widths and lengths as those of the front-side positive traces 2Ps, 2Pm, and 2Pl on the front side. With this arrangement, the resistances applied to LED chips 4 connected to the front-side positive traces 2Ps, 2Pm, and 2Pl are about 3.8Ω, 0.625δ, and 0.2Ω, respectively. Accordingly, the values of electric current passing through these LED chips 4 when a voltage of 2.5 V is applied are about 50 mA, 80 mA, and 100 mA, respectively. As such, in the irradiation substrate in accordance with Embodiment 4, the irradiation intensity at every position including the four corners of the irradiation substrate was successfully included within the range of from the maximum value to 80%. It was verified that the arrangement of Embodiment 4 provides the same effects as those of Embodiment 1.

Embodiment 5

Figure 16:
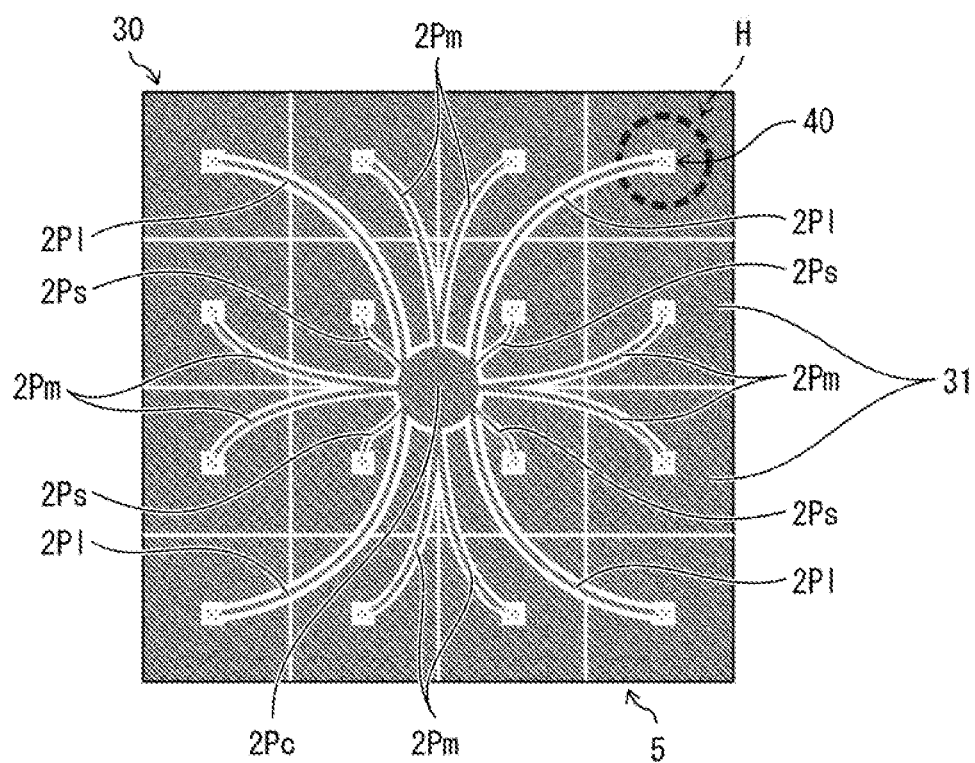
FIG. 16 is a front view schematically illustrating a configuration of an irradiation substrate in accordance with Embodiment 5.

Embodiment 5 is a variation of Embodiment 3. FIG. 16 is a front view schematically illustrating a configuration of an irradiation substrate in accordance with Embodiment 5.

Embodiment 5 is different from Embodiment 3 in that, as illustrated in FIG. 16, dummy traces 31 are provided to the flexible substrate 5 of the irradiation substrate 1 in addition to the front-side positive traces 2Pl, 2Pm, and 2Ps. Since the dummy traces 31 are added to the front side of the flexible substrate 5, the exposed area of the front surface of the flexible substrate 5 is reduced, and the proportion of the covered area of the front surface of the flexible substrate 5 is increased.

The front-side positive traces 2Pl, 2Pm, and 2Ps are not changed from those described in Embodiment 3 with reference to FIG. 11, and therefore the emission intensity of each LED chip 4 is not so different from that of Embodiment 3. Note, however, that the exposed area of the front surface of the flexible substrate 5 is reduced because of the dummy traces 31. Therefore, an inexpensive flexible substrate with low reflectivity can be used. Accordingly, costs for the irradiation substrate can be reduced. Furthermore, since the dummy traces 31 are electrically insulated, even if the dummy traces 31 make contact with the traces (back-side negative traces 9Ns, 9Nm, and 9Nl) on the back side of the flexible substrate 5 when the substrate is cut into a shape that matches the shape of a treatment target area or the like, electric short-circuits will be prevented.

It should be understood that the same effects as described above can also be achieved by adding dummy traces 31 to the foregoing Embodiment 4.

It was verified that the arrangement of Embodiment 5 provides similar effects to those of Embodiment 1.

Embodiment 6

Embodiment 6 is a combination of Embodiment 1 and Embodiment 4. The flexible substrate 5 and traces on the front side of the flexible substrate 5 are the same in material and pattern as those of Embodiment 1 illustrated in FIGS. 1 and 2. On the other hand, the traces on the back side of the flexible substrate 5 are the same as those of Embodiment 4, except for the thicknesses and widths of the traces.

The front surface of the flexible substrate 5 is provided with an allover front-side positive trace 2P described in Embodiment 1, and therefore the front surface of the flexible substrate 5 is covered. Therefore, the reflectivity of the front surface of the flexible substrate 5 is not an issue here and an inexpensive film material can be used for the flexible substrate 5.

On the back side of the flexible substrate 5, individual traces (back-side negative traces 9Ns, 9Nm, and 9Nl) are provided for respective LED chips 4. Thus, the widths of the respective traces can be adjusted and thereby the electric resistances of the traces (back-side negative traces 9Ns, 9Nm, and 9Nl) connected to the respective LED chips 4 can be controlled. Note, however, that, in order to avoid electrical short-circuit defects that would occur when the substrate is cut into a shape that matches the shape of a treatment target area or the like, the thicknesses of the back-side negative traces 9Ns, 9Nm, and 9Nl should inevitably be smaller and are half (5 μm) of that of Embodiment 4.

The lengths of the back-side negative traces 9Ns, 9Nm, and 9Nl are 2.1 mm, 6.1 mm, and 9.4 mm, respectively, which are the same as those of Embodiment 4. The widths of the traces are set as 5.1 μm, 50 μm, and 448 μm. A reason why the set widths of the traces are different from those of Embodiment 4 is that, although the LED chips 4 used in Embodiment 4 are LEDs that emit red light, the LED chips 4 used in Embodiment 6 are LEDs that emit blue-violet light, and therefore the LED chips 4 in Embodiment 6 have different current-voltage characteristics from those of Embodiment 4 and thus resistance settings should be changed. In Embodiment 4, the resistance of the traces is the same between the front and back sides of the flexible substrate 5; however, in Embodiment 6, the resistance of the traces on the front side of the flexible substrate 5 is substantially ignorable, and therefore the resistance of the traces on the back side is dominant. Since the thickness of the traces is halved, the resistance of the traces on the back side of the flexible substrate 5 is twice that of Embodiment 4. After all, the resistance of the traces applied to the LED chips 4 is not different from an arrangement in which individual traces are provided to respective LED chips 4 on each of the front and back sides of the flexible substrate 5.

Not only the foregoing combination of Embodiment 1 and Embodiment 4, but also a combination of Embodiment 1 and Embodiment 3, can be employed similarly.

It was verified that the arrangement of Embodiment 6 provides similar effects to those of Embodiment 2.

Embodiment 7

Figure 17:
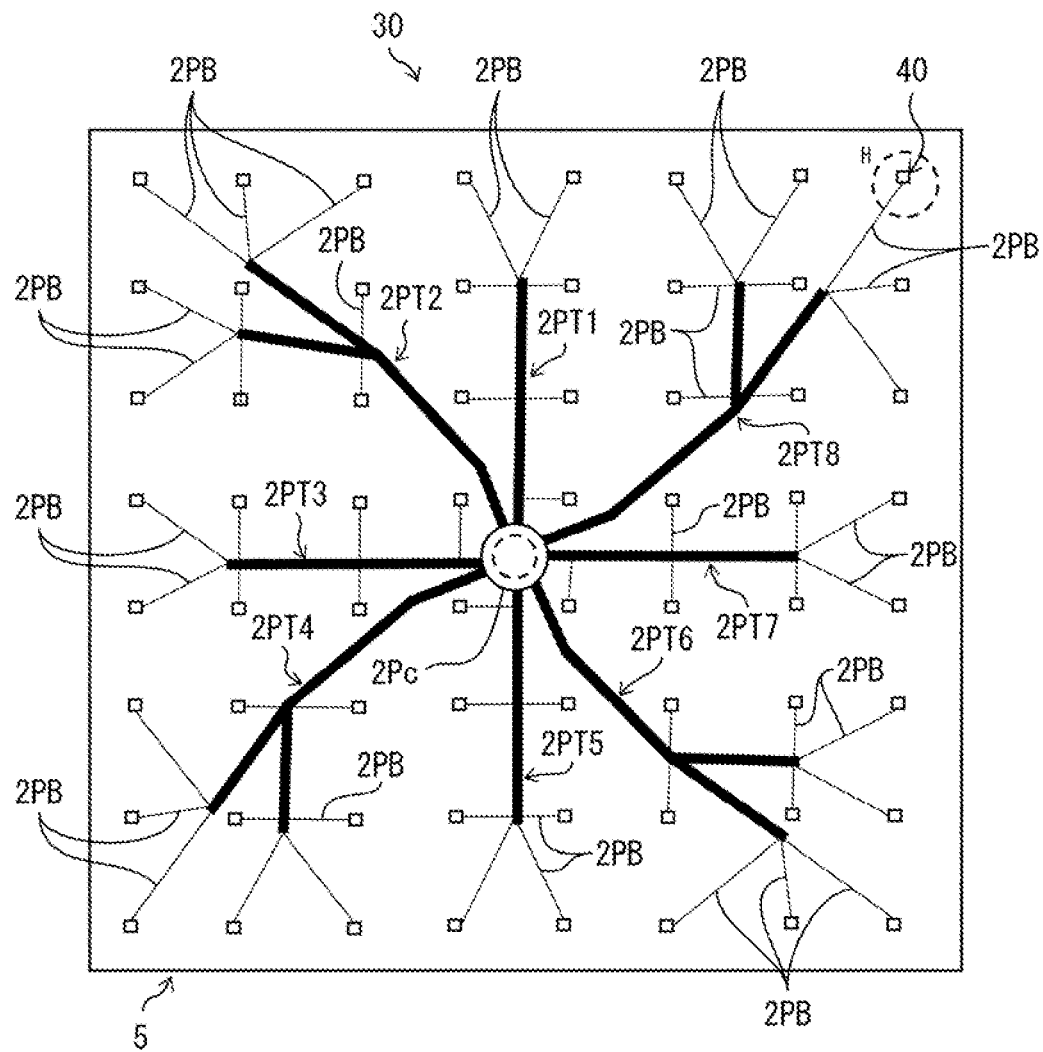
FIG. 17 is a front view schematically illustrating a configuration of an irradiation substrate in accordance with Embodiment 7.
Figure 18:
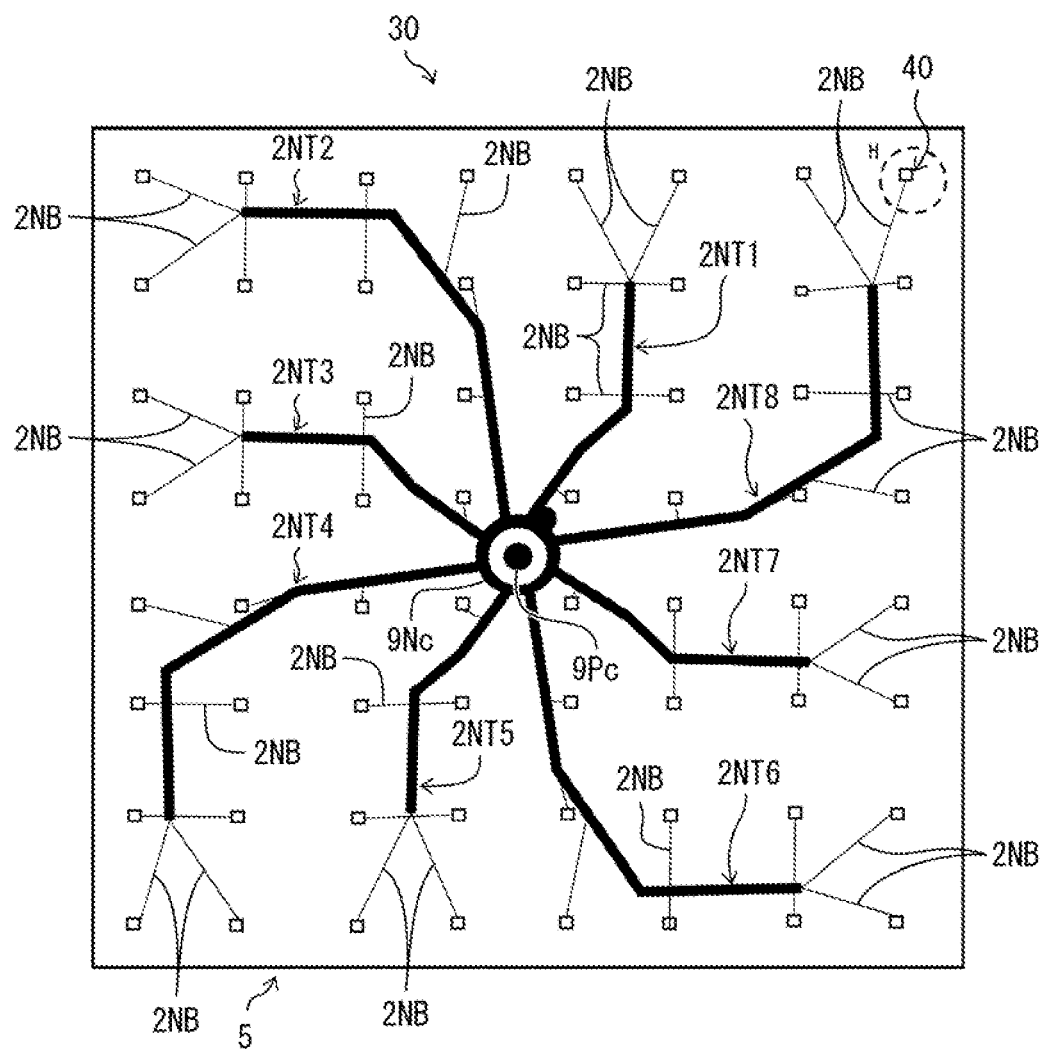
FIG. 18 is a backside perspective view schematically illustrating the configuration of the irradiation substrate.

Embodiment 7 is a variation of Embodiment 3. FIG. 17 is a front view schematically illustrating a configuration of an irradiation substrate 30 in accordance with Embodiment 7. FIG. 18 is a backside perspective view schematically illustrating the configuration of the irradiation substrate 30 in accordance with Embodiment 7.

Embodiment 7 is different from Embodiment 3 in that, as illustrated in FIG. 17, front-side positive traces on the flexible substrate 5 of the irradiation substrate 30 are constituted by: front-side positive main traces 2PT1 to 2PT8 (main traces); and front-side positive branch traces 2PB (branch traces) connecting the front-side positive main traces 2PT1 to 2PT8 and LED chip placement areas 40.

Similarly, as illustrated in FIG. 18, back-side negative traces are constituted by: back-side negative main traces 2NT1 to 2NT8; and back-side negative branch traces 2NB connecting the back-side negative main traces 2NT1 to 2NT8 and the LED chip placement areas 40.

In the example shown in FIGS. 17 and 18, sixty-four LED chip placement areas 40 in 8 rows×8 columns are mounted on the irradiation substrate 30. When the number of LED chips 4 mounted on the irradiation substrate 30 increases, the traces near the center of the irradiation substrate 30 become too dense and it is sometimes difficult to provide individual traces to connect the LED chips 4 to the front-side central positive trace 2Pc like FIG. 11. In such a case, by dividing the traces into the main traces (front-side positive main traces 2PT1 to 2PT8) and the branch traces (front-side positive branch traces 2PB) like the arrangement of Embodiment 7, the traces can be easily routed and the density of traces near the center is prevented from increasing. The same applies to the back side of the irradiation substrate 30.

It is preferable that the resistance value between the front-side central positive trace 2Pc and each LED chip 4 is substantially equal among the LED chips 4. Therefore, each front-side positive branch trace 2PB is preferably changed in width depending on the distance from the front-side central positive trace 2Pc thereto and the length thereof. In a case where the width of each of the front-side positive main traces 2PT1 to 2PT8 is sufficiently greater than that of the front-side positive branch traces 2PB, the resistance value between the front-side central positive trace 2Pc and each LED chip 4 is determined by the resistance value of a corresponding front-side positive branch trace 2PB. Therefore, the width of the front-side positive branch trace 2PB is substantially proportional to the length of the front-side positive branch trace 2PB.

The same applies to the resistance value between the back-side central negative trace 9Nc and each LED chip 4. Each back-side negative branch trace 2NB is preferably changed in width depending on the distance from the back-side central negative trace 9Nc thereto and the length thereof. In a case where the width of each of the back-side negative main traces 2NT1 to 2NT8 is sufficiently greater than that of the back-side negative branch traces 2NB, the resistance value between the back-side central negative trace 9Nc and each LED chip 4 is determined by the resistance of a corresponding back-side negative branch trace 2NB. Therefore, the width of the back-side negative branch trace 2NB is substantially proportional to the length of the back-side negative branch trace 2NB.

In Embodiment 3, the front-side positive traces 2Ps, 2Pm, and 2Pl and the back-side negative traces 2Ns, 2Nm, and 2Nl are arranged so as not to overlap each other; however, in a case where the number of LED chips N is large like Embodiment 7, it is sometimes difficult to arrange the front-side traces and back-side traces such that they do not overlap each other at all. In such causes, the overlapping is preferably minimized. It is preferable that at least the front-side positive main traces 2PT1 to 2PT8 and the back-side negative main traces 2NT1 to 2NT8 do not overlap each other.

In Embodiment 3 illustrated in FIG. 11, the front-side positive traces 2Ps, 2Pm, and 2Pl do not share any of their portions and are totally individual traces. However, in Embodiment 7, some of the traces connecting the front-side central positive trace 2Pc and the LED chips 4 share the front-side positive main traces 2PT1 to 2PT8, whereas the front-side positive branch traces 2PB are totally individual traces. In this sense, the traces connecting front-side central positive trace 2Pc and the LED chips 4 are partially individual traces. Even though they are partially individual traces, the resistance value of each trace can be adjusted by adjusting the length and width of the front-side positive branch traces 2PB. Thus, in regard to resistance adjustment function, Embodiment 7 achieves the same effects as Embodiment 3. The same applies to the back-side traces illustrated in FIG. 18. Furthermore, also in Embodiment 7, the front-side traces and the back-side traces are prevented from overlapping, except some intersections. As such, the individual traces are not limited to totally individual traces.

It should be understood that the same effects as described in Embodiment 5 can also be achieved by adding, to Embodiment 7, dummy traces 31 described in Embodiment 5 and illustrated in FIG. 16.

It was verified that also the arrangement of Embodiment 7 provides similar effects to those of Embodiment 1.

As has been described, Embodiments 1 to 7 are suitable for a relatively small treatment target area, and it is possible to apply light in a substantially uniform manner even to a nonflat treatment target area. Since Embodiments 1 to 7 achieve effective and uniform irradiation while minimizing side effects that would be caused by the irradiation, it is possible to achieve phototherapeutic effect with less burden on a patient and his/her family.

[Recap]

An irradiation substrate (1, 23, 30) in accordance with Aspect 1 of the present invention includes: a trace (front-side positive trace 2P, front-side negative trace 2N, front-side positive traces 2Ps, 2Pm, and 2Pl, front-and-back connecting portion 8, back-side negative trace 9N, back-side negative traces 9Ns, 9Nm, and 9Nl) disposed on a flexible substrate (5); an electric power supply part (positive external connection line 12P, negative external connection line 12N, back-side positive trace 9P, front-side central positive trace 2Pc, back-side central positive trace 9Pc, back-side central negative trace 9Nc) connected to the trace (front-side positive trace 2P, front-side negative trace 2N, front-side positive traces 2Ps, 2Pm, and 2Pl, front-and-back connecting portion 8, back-side negative trace 9N, back-side negative traces 9Ns, 9Nm, and 9Nl) to externally supply electric power; and LED chips (4) disposed on a front side of the flexible substrate (5) and connected to the trace (front-side positive trace 2P, front-side negative trace 2N, front-side positive traces 2Ps, 2Pm, and 2Pl, front-side negative trace 2N), wherein an electric resistance between the electric power supply part (positive external connection line 12P, negative external connection line 12N, back-side positive trace 9P, front-side central positive trace 2Pc, back-side central positive trace 9Pc, back-side central negative trace 9Nc) and one of the LED chips (4) which is farthest from the electric power supply part (positive external connection line 12P, negative external connection line 12N, back-side positive trace 9P, front-side central positive trace 2Pc, back-side central positive trace 9Pc, back-side central negative trace 9Nc) is less than an internal resistance of the one of the LED chips (4) which is farthest from the electric power supply part.

According to the above arrangement, the electric resistance between the electric power supply part and one of the LED chips which is farthest from the electric power supply part is less than the internal resistance of the one of the LED chips which is farthest from the electric power supply part. Therefore, the internal resistance of each LED chip has a dominantly greater value than the electric resistance between each LED chip and the electric power supply part. This reduces the effect of the electric resistance between each LED chip and the electric power supply part which varies depending on the distance from each LED chip to the electric power supply part, and reduces variations in emission intensity among the LED chips disposed on the front side of the flexible substrate. This makes it possible to bring the irradiation intensity of the LED chips disposed on the front side of the flexible substrate closer to uniformity.

An irradiation substrate (1, 23, 30) in accordance with Aspect 2 of the present invention may be arranged such that, in Aspect 1, the electric resistance is not greater than one-tenth of the internal resistance.

The above arrangement further reduces the effect of the electric resistance between each LED chip and the electric power supply part which varies depending on the distance from each LED chip to the electric power supply part, and further reduces variations in emission intensity among the LED chips disposed on the front side of the flexible substrate. This makes it possible to bring the irradiation intensity of the LED chips disposed on the front side of the flexible substrate even closer to uniformity.

An irradiation substrate (30) in accordance with Aspect 3 of the present invention may be arranged such that, in Aspect 1 or 2: the trace includes a front-side trace part (front-side positive traces 2Ps, 2Pm, and 2Pl, front-side negative trace 2N) and a back-side trace part (back-side negative traces 9Ns, 9Nm, and 9Nl), the front-side trace part being disposed on the front side of the flexible substrate (5), the back-side trace part being disposed on a back side of the flexible substrate (5); the electric power supply part (positive external connection line 12P, negative external connection line 12N, back-side central positive trace 9Pc, back-side central negative trace 9Nc) is disposed on the back side of the flexible substrate (5), and the electric power supply part (front-side central positive trace 2Pc) is disposed on the front side of the flexible substrate (5); and at least one of the front-side trace part (front-side positive traces 2Ps, 2Pm, and 2Pl, front-side negative trace 2N) and the back-side trace part (back-side negative traces 9Ns, 9Nm, and 9Nl) includes individual traces (front-side positive traces 2Ps, 2Pm, and 2Pl, back-side negative traces 9Ns, 9Nm, and 9Nl) that extend from the electric power supply part (front-side central positive trace 2Pc, back-side central negative trace 9Nc) to individually connect to the respective LED chips (4).

According to the above arrangement, the individual traces are provided which extend from the electric power supply part to individually connect to the respective LED chips. This makes it possible to individually control the electric resistance from each LED chip to the electric power supply part.

An irradiation substrate (1, 23) in accordance with Aspect 4 of the present invention may be arranged such that, in Aspect 1 or 2: the trace includes a front-side trace part (front-side positive trace 2P) and a back-side trace part (back-side negative trace 9N), the front-side trace part being disposed on the front side of the flexible substrate (5), the back-side trace part being disposed on a back side of the flexible substrate (5); the electric power supply part (positive external connection line 12P, negative external connection line 12N, back-side positive trace 9P) is disposed on the back side of the flexible substrate (5); and at least one of the front-side trace part (front-side positive trace 2P) and the back-side trace part (back-side negative trace 9N) includes an allover trace (front-side positive trace 2P, back-side negative trace 9N) that connects the electric power supply part (positive external connection line 12P, negative external connection line 12N, back-side positive trace 9P) and the LED chips (4) collectively.

According to the above arrangement, at least one of the front-side trace part and the back-side trace part includes the allover trace, which connects the electric power supply part and the LED chips collectively. This makes it possible to reduce the electric resistance between each LED chip and the electric power supply part.

An irradiation substrate (1, 23, 30) in accordance with Aspect 5 of the present invention includes: a trace (front-side positive trace 2P, front-side positive traces 2Ps, 2Pm, and 2Pl, front-side negative trace 2N, back-side negative trace 9N, back-side negative traces 9Ns, 9Nm, and 9Nl) disposed on a flexible substrate (5); an electric power supply part (positive external connection line 12P, negative external connection line 12N, back-side positive trace 9P, front-side central positive trace 2Pc, back-side central positive trace 9Pc, back-side central negative trace 9Nc) connected to the trace (front-side positive trace 2P, front-side positive traces 2Ps, 2Pm, and 2Pl, front-side negative trace 2N, back-side negative trace 9N, back-side negative traces 9Ns, 9Nm, and 9Nl, back-side positive trace 9P) to externally supply electric power; and LED chips (4) provided to the flexible substrate (5) and connected to the trace (front-side positive trace 2P, front-side positive traces 2Ps, 2Pm, and 2Pl, front-side negative trace 2N, back-side negative trace 9N, back-side negative traces 9Ns, 9Nm, and 9Nl), wherein the LED chips 4 are substantially equal to each other in electric resistance between itself and the electric power supply part (positive external connection line 12P, negative external connection line 12N, back-side positive trace 9P, front-side central positive trace 2Pc, back-side central positive trace 9Pc, back-side central negative trace 9Nc).

According to the above arrangement, the LED chips are substantially equal to each other in electric resistance between itself and the electric power supply part. Therefore, substantially equal amounts of electric current pass through the LED chips. This makes it possible to bring the emission intensity of the LED chips of the irradiation substrate closer to uniformity.

An irradiation substrate (1, 23, 30) in accordance with Aspect 6 of the present invention may be arranged such that, in Aspect 5, an electric resistance between the electric power supply part (positive external connection line 12P, negative external connection line 12N, back-side positive trace 9P, front-side central positive trace 2Pc, back-side central positive trace 9Pc, back-side central negative trace 9Nc) and one of the LED chips (4) which is farthest from the electric power supply part (positive external connection line 12P, negative external connection line 12N, back-side positive trace 9P, front-side central positive trace 2Pc, back-side central positive trace 9Pc, back-side central negative trace 9Nc) is not greater than one-tenth of an internal resistance of the one of the LED chips (4) which is farthest from the electric power supply part.

The above arrangement reduces the effect of the electric resistance between each LED chip and the electric power supply part, and further reduces variations in emission intensity among the LED chips disposed on the front side of the flexible substrate.

An irradiation substrate (1, 23, 30) in accordance with Aspect 7 of the present invention may be arranged such that, in Aspect 5 or 6: the trace includes a front-side trace part (front-side positive trace 2P, front-side positive traces 2Ps, 2Pm, and 2Pl, front-side negative trace 2N) and a back-side trace part (back-side negative trace 9N, back-side negative traces 9Ns, 9Nm, and 9Nl), the front-side trace part being disposed on a front side of the flexible substrate (5), the back-side trace part being disposed on a back side of the flexible substrate (5); the electric power supply part (positive external connection line 12P, negative external connection line 12N, back-side positive trace 9P, back-side central positive trace 9Pc, back-side central negative trace 9Nc) is disposed on the back side of the flexible substrate (5); and at least one of the front-side trace part (front-side positive trace 2P, front-side positive traces 2Ps, 2Pm, and 2Pl) and the back-side trace part (back-side negative trace 9N, back-side negative traces 9Ns, 9Nm, and 9Nl) includes individual traces (front-side positive traces 2Ps, 2Pm, and 2Pl, back-side negative traces 9Ns, 9Nm, and 9Nl) that extend from the electric power supply part (positive external connection line 12P, negative external connection line 12N, front-side central positive trace 2Pc, back-side central negative trace 9Nc) to individually connect to the respective LED chips (4).

According to the above arrangement, it is possible to individually control the electric resistance from each LED chip to the electric power supply part.

An irradiation substrate (1, 23, 30) in accordance with Aspect 8 of the present invention may be arranged such that, in Aspect 5 or 6: the trace includes a front-side trace part and a back-side trace part, the front-side trace part being disposed on a front side of the flexible substrate (5), the back-side trace part being disposed on a back side of the flexible substrate (5); the electric power supply part (positive external connection line 12P, negative external connection line 12N, back-side positive trace 9P, back-side central positive trace 9Pc, back-side central negative trace 9Nc) is disposed on the back side of the flexible substrate (5) and the electric power supply part (front-side central positive trace 2Pc) is disposed on the front side of the flexible substrate (5); and at least one of the front-side trace part and the back-side trace part includes an allover trace (front-side positive trace 2P, back-side negative trace 9N) that connects the electric power supply part (positive external connection line 12P, negative external connection line 12N, back-side positive trace 9P, front-side central positive trace 2Pc, back-side central positive trace 9Pc, back-side central negative trace 9Nc) and the LED chips (4) collectively.

According to the above arrangement, at least one of the front-side trace part and the back-side trace part includes the allover trace, which connects the electric power supply part and the LED chips collectively. This makes it possible to reduce the electric resistance between each LED chip and the electric power supply part.

An irradiation substrate (1, 23, 30) in accordance with Aspect 9 of the present invention includes: a trace (front-side positive trace 2P, front-side positive traces 2Ps, 2Pm, and 2Pl, front-side negative trace 2N, back-side negative trace 9N, back-side negative traces 9Ns, 9Nm, and 9Nl) disposed on a flexible substrate (5); an electric power supply part (positive external connection line 12P, negative external connection line 12N, back-side positive trace 9P, front-side central positive trace 2Pc, back-side central positive trace 9Pc, back-side central negative trace 9Nc) connected to the trace (front-side positive trace 2P, front-side positive traces 2Ps, 2Pm, and 2Pl, front-side negative trace 2N, back-side negative trace 9N, back-side negative traces 9Ns, 9Nm, and 9Nl) to externally supply electric power; and LED chips (4) provided to the flexible substrate (5) and connected to the trace (front-side positive trace 2P, front-side positive traces 2Ps, 2Pm, and 2Pl, front-side negative trace 2N), wherein an electric resistance between the electric power supply part (positive external connection line 12P, negative external connection line 12N, back-side positive trace 9P, front-side central positive trace 2Pc, back-side central positive trace 9Pc, back-side central negative trace 9Nc) and one of the LED chips (4) which is disposed near a center of the flexible substrate (5) is greater than an electric resistance between the electric power supply part (positive external connection line 12P, negative external connection line 12N, back-side positive trace 9P, front-side central positive trace 2Pc, back-side central positive trace 9Pc, back-side central negative trace 9Nc) and another one of the LED chips (4) which is disposed near a periphery of the flexible substrate (5).

According to the above arrangement, the electric resistance between the electric power supply part and one of the LED chips which is disposed near the center of the flexible substrate is greater than the electric resistance between the electric power supply part and another one of the LED chips which is disposed near the periphery of the flexible substrate. Therefore, the emission intensity of the LED chip near the periphery, at which irradiation intensity would otherwise be inevitably weaker than that near the center because there are no LED chips outside the periphery, is greater than the LED chip near the center and thereby uniformity of irradiation intensity in the flexible substrate is improved.

An irradiation substrate (1, 23, 30) in accordance with Aspect 10 of the present invention may be arranged such that, in Aspect 9, the electric resistance between the electric power supply part (positive external connection line 12P, negative external connection line 12N, back-side positive trace 9P, front-side central positive trace 2Pc, back-side central positive trace 9Pc, back-side central negative trace 9Nc) and the one of the LED chips (4) which is disposed near the periphery of the flexible substrate (5) is not greater than one-tenth of an internal resistance of the one of the LED chips (4) which is disposed near the periphery of the flexible substrate (5).

The above arrangement reduces the effect of the electric resistance between each LED chip and the electric power supply part, and further reduces variations in emission intensity among the LED chips disposed on the front side of the flexible substrate.

An irradiation substrate (30) in accordance with Aspect 11 of the present invention may be arranged such that, in Aspect 9 or 10: the trace includes a front-side trace part (front-side positive traces 2Ps, 2Pm, and 2Pl, front-side negative trace 2N) and a back-side trace part (9Ns, 9Nm, and 9Nl), the front-side trace part being disposed on a front side of the flexible substrate (5), the back-side trace part being disposed on a back side of the flexible substrate (5); the electric power supply part (positive external connection line 12P, negative external connection line 12N, front-side central positive trace 2Pc, back-side central positive trace 9Pc, back-side central negative trace 9Nc) is disposed on the back side of the flexible substrate 5; and at least one of the front-side trace part (front-side positive traces 2Ps, 2Pm, and 2Pl, front-side negative trace 2N) and the back-side trace part (9Ns, 9Nm, and 9Nl) includes individual traces (front-side positive traces 2Ps, 2Pm, and 2Pl, back-side negative traces 9Ns, 9Nm, and 9Nl) that extend from the electric power supply part (positive external connection line 12P, negative external connection line 12N, front-side central positive trace 2Pc, back-side central positive trace 9Pc, back-side central negative trace 9Nc) to individually connect to the respective LED chips (4).

According to the above arrangement, it is possible to individually control the electric resistance from each LED chip to the electric power supply part.

An irradiation substrate (1, 23) in accordance with Aspect 12 of the present invention may be arranged such that, in Aspect 9 or 10: the trace includes a front-side trace part (front-side positive trace 2P, front-side negative trace 2N) and a back-side trace part (back-side negative trace 9N, back-side positive trace 9P), the front-side trace part being disposed on a front side of the flexible substrate (5), the back-side trace part being disposed on a back side of the flexible substrate (5); the electric power supply part (positive external connection line 12P, negative external connection line 12N, back-side positive trace 9P) is disposed on the back side of the flexible substrate (5); and at least one of the front-side trace part (front-side positive trace 2P) and the back-side trace part (back-side negative trace 9N) includes an allover trace that connects the electric power supply part (positive external connection line 12P, negative external connection line 12N, back-side positive trace 9P) and the LED chips (4) collectively.

According to the above arrangement, it is possible to reduce the electric resistance between each LED chip and the electric power supply part.

An irradiation substrate (30) in accordance with Aspect 13 of the present invention may be arranged such that, in any one of Aspects 3, 7, and 11: both the front-side trace part (front-side positive traces 2Ps, 2Pm, and 2Pl) and the back-side trace part (back-side negative traces 9Ns, 9Nm, and 9Nl) each include the individual traces that extend from the electric power supply part (positive external connection line 12P, negative external connection line 12N, front-side central positive trace 2Pc, back-side central negative trace 9Nc) to individually connect to the respective LED chips (4); and the individual traces of the front-side trace part (front-side positive traces 2Ps, 2Pm, and 2Pl) and the individual traces of the back-side trace part (back-side negative traces 9Ns, 9Nm, and 9Nl) are routed so as not to overlap each other.

According to the above arrangement, it is possible to prevent short-circuit defects between the front-side trace part and the back-side trace part that would otherwise occur when the substrate is cut into a shape that matches the shape of a treatment target area.

An irradiation substrate (1, 23, 30) in accordance with Aspect 14 of the present invention may be arranged such that, in any one of Aspects 1 to 13, the trace is thinner than the flexible substrate.

According to the above arrangement, it is possible to prevent short-circuit defects between traces that would otherwise occur when the substrate is cut into a shape that matches the shape of a treatment target area.

An irradiation substrate (30) in accordance with Aspect 15 of the present invention may be arranged such that, in Aspect 5, the trace includes: a main trace (front-side positive main traces 2PT1 to 2PT8, back-side negative main traces 2NT1 to 2NT8) shared by at least two of the LED chips (4); and branch traces (front-side positive branch traces 2PB, back-side negative branch traces 2NB) provided for the respective LED chips (4).

According to the above arrangement, even when the number of LED chips mounted on the irradiation substrate increases, density of traces near the center of the irradiation substrate does not increase much.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

Reference Signs List

1, 23, 30 Irradiation substrate
2P Front-side positive trace (trace, front-side trace part, allover trace)
2N Front-side negative trace (trace, front-side trace part, allover trace)
2Ps, 2Pm, 2Pl Front-side positive trace (trace, front-side trace part, individual trace)
2Pc Front-side central positive trace (electric power supply part)
2PT1 to 2PT8 Front-side positive main trace (main trace)
2PB Front-side positive branch trace (branch trace)
2NT1 to 2NT8 Back-side negative main trace (main trace)
2NB Back-side negative branch trace (branch trace)
4 LED chip
5 Flexible substrate
8 Front-and-back connecting portion (trace)
9P Back-side positive trace (electric power supply part)
9N Back-side negative trace (trace, back-side trace part, allover trace)
9Ns, 9Nm, 9Nl Back-side negative trace (trace, back-side trace part, individual trace)
9Nc Back-side central negative trace (electric power supply part)
9Pc Back-side central positive trace (electric power supply part)
12P Positive external connection line (electric power supply part)
12N Negative external connection line (electric power supply part)
15 Chip resistor

The invention claimed is:

1. An irradiation substrate, comprising:
a trace disposed on a flexible substrate;
an electric power supply part connected to the trace at a center of the flexible substrate to externally supply electric power; and
LED chips disposed on a front side of the flexible substrate and connected to the trace,
wherein:
the trace includes a front-side trace part and a back-side trace part, the front-side trace part being disposed on the front side of the flexible substrate, the back-side trace part being disposed on a back side of the flexible substrate;
the electric power supply part is disposed on the back side of the flexible substrate;
the flexible substrate has a connecting hole at the center;
the front-side trace part is disposed so as to connect to the electric power supply part through the connecting hole; and
an electric resistance between the electric power supply part and one of the LED chips which is farthest from the electric power supply part is less than an internal resistance of the one of the LED chips which is farthest from the electric power supply part.

2. The irradiation substrate according to claim 1, wherein the electric resistance is not greater than one-tenth of the internal resistance.

3. The irradiation substrate according to claim 1, wherein at least one of the front-side trace part and the back-side trace part includes individual traces that extend from the electric power supply part to individually connect to the respective LED chips.

4. The irradiation substrate according to claim 3, wherein:
both the front-side trace part and the back-side trace part each include the individual traces that extend from the electric power supply part to individually connect to the respective LED chips; and
the individual traces of the front-side trace part and the individual traces of the back-side trace part are routed so as not to overlap each other.

5. The irradiation substrate according to claim 1, wherein at least one of the front-side trace part and the back-side trace part includes an allover trace that connects the electric power supply part and the LED chips collectively.

6. The irradiation substrate according to claim 1, wherein the trace is thinner than the flexible substrate.

7. An irradiation substrate, comprising:
a trace disposed on a flexible substrate;
an electric power supply part connected to the trace at a center of the flexible substrate to externally supply electric power; and
LED chips provided to the flexible substrate and connected to the trace,
wherein the LED chips are substantially equal to each other in electric resistance between itself and the electric power supply part.

8. The irradiation substrate according to claim 7, wherein an electric resistance between the electric power supply part and one of the LED chips which is farthest from the electric power supply part is not greater than one-tenth of an internal resistance of the one of the LED chips which is farthest from the electric power supply part.

9. The irradiation substrate according to claim 7, wherein:
the trace includes a front-side trace part and a back-side trace part, the front-side trace part being disposed on a front side of the flexible substrate, the back-side trace part being disposed on a back side of the flexible substrate;
the electric power supply part is disposed on the back side of the flexible substrate; and
at least one of the front-side trace part and the back-side trace part includes individual traces that extend from the electric power supply part to individually connect to the respective LED chips.

10. The irradiation substrate according to claim 9, wherein:
both the front-side trace part and the back-side trace part each include the individual traces that extend from the electric power supply part to individually connect to the respective LED chips; and
the individual traces of the front-side trace part and the individual traces of the back-side trace part are routed so as not to overlap each other.

11. The irradiation substrate according to claim 7, wherein:
the trace includes a front-side trace part and a back-side trace part, the front-side trace part being disposed on a front side of the flexible substrate, the back-side trace part being disposed on a back side of the flexible substrate;
the electric power supply part is disposed on the back side of the flexible substrate; and
at least one of the front-side trace part and the back-side trace part includes an allover trace that connects the electric power supply part and the LED chips collectively.

12. The irradiation substrate according to claim 7, wherein the trace includes: a main trace shared by at least two of the LED chips; and branch traces provided for the respective LED chips.

13. The irradiation substrate according to claim 7, wherein the trace is thinner than the flexible substrate.

14. An irradiation substrate, comprising:
a trace disposed on a flexible substrate;
an electric power supply part connected to the trace at a center of the flexible substrate to externally supply electric power; and
LED chips provided to the flexible substrate and connected to the trace,
wherein an electric resistance between the electric power supply part and one of the LED chips which is disposed near the center of the flexible substrate is greater than an electric resistance between the electric power supply part and another one of the LED chips which is disposed near a periphery of the flexible substrate.

15. The irradiation substrate according to claim 14, wherein the electric resistance between the electric power supply part and the one of the LED chips which is disposed near the periphery of the flexible substrate is not greater than one-tenth of an internal resistance of the one of the LED chips which is disposed near the periphery of the flexible substrate.

16. The irradiation substrate according to claim 14, wherein:
the trace includes a front-side trace part and a back-side trace part, the front-side trace part being disposed on a front side of the flexible substrate, the back-side trace part being disposed on a back side of the flexible substrate;
the electric power supply part is disposed on the back side of the flexible substrate; and
at least one of the front-side trace part and the back-side trace part includes individual traces that extend from the electric power supply part to individually connect to the respective LED chips.

17. The irradiation substrate according to claim 16, wherein:
both the front-side trace part and the back-side trace part each include the individual traces that extend from the electric power supply part to individually connect to the respective LED chips; and
the individual traces of the front-side trace part and the individual traces of the back-side trace part are routed so as not to overlap each other.

18. The irradiation substrate according to claim 14, wherein:
the trace includes a front-side trace part and a back-side trace part, the front-side trace part being disposed on a front side of the flexible substrate, the back-side trace part being disposed on a back side of the flexible substrate;
the electric power supply part is disposed on the back side of the flexible substrate; and
at least one of the front-side trace part and the back-side trace part includes an allover trace that connects the electric power supply part and the LED chips collectively.

19. An irradiation substrate, comprising:
a trace disposed on a flexible substrate;

an electric power supply part connected to the trace at a center of the flexible substrate to externally supply electric power; and LED chips disposed on a front side of the flexible substrate and connected to the trace, wherein:

an electric resistance between the electric power supply part and one of the LED chips which is farthest from the electric power supply part is less than an internal resistance of the one of the LED chips which is farthest from the electric power supply part;

the trace includes a front-side trace part and a back-side trace part, the front-side trace part being disposed on the front side of the flexible substrate, the back-side trace part being disposed on a back side of the flexible substrate;

the electric power supply part is disposed on the back side of the flexible substrate; and at least one of the front-side trace part and the back-side trace part includes an allover trace that connects the electric power supply part and the LED chips collectively.

* * * * *